(12) United States Patent
Hasegawa et al.

(10) Patent No.: US 6,371,907 B1
(45) Date of Patent: *Apr. 16, 2002

(54) ENDOSCOPE APPARATUS DRIVING MANIPULATION WIRES WITH DRIVE MOTOR IN DRUM PORTION

(75) Inventors: Hiroshi Hasegawa, Oume; Takakazu Ishigami, Tama; Nobuyuki Motoki, Hino; Yutaka Konomura, Tachikawa, all of (JP)

(73) Assignee: Olympus Optical Co., Ltd., Tokyo (JP)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 5 days.

(21) Appl. No.: 09/133,326

(22) Filed: Aug. 13, 1998

Related U.S. Application Data

(63) Continuation-in-part of application No. 08/968,579, filed on Nov. 13, 1997, now Pat. No. 6,036,636.

(30) Foreign Application Priority Data

Nov. 18, 1996 (JP) ................................. 8-306711
Jun. 4, 1997 (JP) ................................. 9-146853

(51) Int. Cl.[7] ........................... A61B 1/005; A61B 1/06
(52) U.S. Cl. ..................... 600/146; 600/152; 600/102; 600/150
(58) Field of Search .................. 600/102, 109, 600/114, 131, 139, 146, 152; 604/280

(56) References Cited

U.S. PATENT DOCUMENTS 4,483,326 A * 11/1984 Yamaka et al. ............. 600/149
4,503,842 A * 3/1985 Takayama ................... 600/152

(List continued on next page.)

FOREIGN PATENT DOCUMENTS

| JP | 1-204014 | 3/1989 |
| JP | 4-081711 | 3/1992 |
| JP | 5-056486 | 8/1993 |
| JP | 9-297270 | 11/1997 |

OTHER PUBLICATIONS

Motoki Nobuyuki, "Industrial Endoscope", Abstract, No. 09297270 A, Nov. 18, 1997, pp. 1–12.

Sakae Takehata, "Endoscope Device", Abstract, No. 4–81711 (A), Mar. 16, 1992, pp. 1–20.

Atsushi Miyazaki, "Endoscope Unit Device", Abstract, No. 61–75315, Apr. 17, 1986, pp. 1–24.

Shuichi Takeyama, "Endoscope Device", Abstract, No. 1–204014 (A), Aug. 16, 1989, pp. 99–105.

*Primary Examiner*—John P. Leubecker
(74) *Attorney, Agent, or Firm*—Pillsbury Winthrop LLP

(57) ABSTRACT

A cylindrical surface on which an insertion portion where a curving portion is provided is wound for containing is formed in a drum portion rotatably supported by a fulcrum. Inside the cylindrical surface, an electric drive unit such as motors moving back and forth manipulation wires transmitting driving forces curving the curving portion is contained. By instructing a curving direction with a joy stick provided through a cable outside the drum portion, the curving portion is curved in a desired direction through the electric drive unit. A monitor displaying an image to be observed through a cable is located outside the drum portion.

36 Claims, 16 Drawing Sheets

U.S. PATENT DOCUMENTS

| | | |
|---|---|---|
| 4,790,624 A | 12/1988 | Van Hoye et al. |
| 4,846,573 A * | 7/1989 | Taylor et al. ............. 356/241.4 |
| 4,884,133 A * | 11/1989 | Kanno et al. .................. 348/68 |
| 4,924,852 A * | 5/1990 | Suzuki et al. ................ 600/150 |
| 4,941,454 A * | 7/1990 | Wood et al. ................. 600/149 |
| 4,941,456 A | 7/1990 | Wood et al. |
| 4,989,582 A * | 2/1991 | Sakiyama et al. .......... 600/109 |
| 5,022,383 A * | 6/1991 | Sakiyama et al. .......... 600/109 |
| 5,060,632 A * | 10/1991 | Hibino et al. ............... 600/109 |
| 5,090,259 A | 2/1992 | Shishido et al. |
| 5,251,611 A | 10/1993 | Zehel et al. |
| 5,271,382 A * | 12/1993 | Chikama .................... 600/142 |
| 5,347,989 A * | 9/1994 | Monroe et al. ............. 600/131 |
| 5,373,317 A | 12/1994 | Salvati et al. |
| 5,439,000 A * | 8/1995 | Gunderson et al. ......... 600/473 |
| 5,522,788 A | 6/1996 | Kuzmak |
| 5,531,664 A * | 7/1996 | Adachi et al. .............. 600/149 |

* cited by examiner

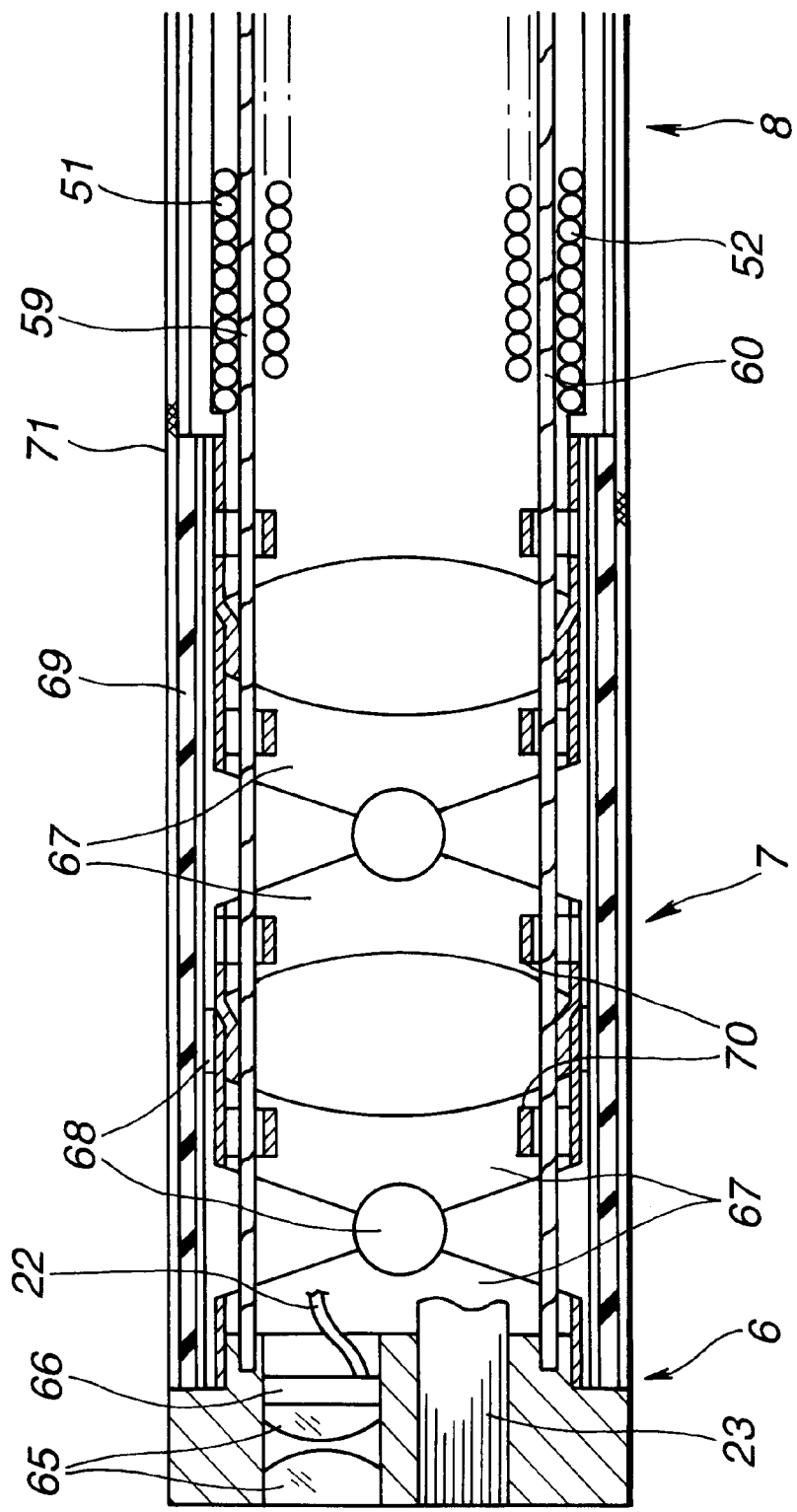

ENDOSCOPE APPARATUS DRIVING MANIPULATION WIRES WITH DRIVE MOTOR IN DRUM PORTION

This is a Continuation-in-part of: National Appln. No. 08/968,579 filed Nov. 13, 1997, now U.S. Pat. No. 6,036,636.

BACKGROUND OF THE INVENTION

1. Field of the Invention

The present invention relates to an endoscope apparatus containing drive motors pulling manipulation wires inside a drum portion winding up an insertion portion where a curving portion is provided.

2. Description of the Related Art

Recently, endoscope apparatuses have widely used in a medical field and an industrial field. In the industrial field, there are endoscope apparatuses that have considerably long insertion portions so that the endoscope apparatuses can be used for observation of the inside of long pipes. In drum-winding types of endoscope apparatuses among them, each insertion portion is wound on a drum so that each endoscope apparatus may become compact when it is not used for an endoscopy.

In this case, it is desirable that the insertion portion is possibly slender to be able to insert the portion into and inspect a pipe and the like with a small inner diameter. In addition, so as to be able to correspond to a case that the insertion portion is inserted into an inside of a desired pipe among plural branched pipes, it is desirable to provide a curving portion at a tip side portion of the insertion portion.

For example, in U.S. Pat. No. 5,090,259, an endoscope apparatus comprising means making an insertion portion self-propel into a pipe is disclosed.

Since, in this prior patent, the means making the insertion portion self-propel and inserting the portion is provided on an outer circumferential surface of the insertion portion, the insertion portion becomes large. Furthermore, since curving is performed by providing artificial muscles on an outer circumferential surface of a tip of the insertion portion, the outer diameter of the insertion portion becomes large. Therefore, this patent has a demerit that the range of objects that this insertion portion can be inserted into and inspect is limited.

SUMMARY OF THE INVENTION

A first object of the present invention is to provide an endoscope apparatus that has a slender insertion portion, secures an easily operable curving function, and can have a compact size when an endoscopy is not performed.

Another object of the present invention is to provide an endoscope apparatus capable of performing the endoscopy simply and quickly.

This endoscope apparatus of the present invention comprises:

a slender, flexible insertion portion that has a curving portion free to be curved and can be inserted into a lumen;

an illumination optical system emitting illumination light and an imaging optical system imaging a subject illuminated by the illumination optical system, both of which are provided in a tip portion of the insertion portion;

a drum portion that the proximal end of the insertion portion is connected to and a take-up portion, where the insertion portion is wound up, is provided in;

manipulation wires that are inserted in an axial direction of the insertion portion and make the curving portion curve by moving to the axial direction;

drive motors that are provided in the drum portion and makes the curving portion curve by moving the manipulation wires; and curving manipulation means for performing curving manipulation of the curving portion by controlling drive operation of the drive motors. This endoscope apparatus realizes a slender curving portion by adopting the construction of curving the curving portion by moving the manipulation wires, and secures light curving manipulation by moving the manipulation wires with the drive motors through the operation with the curving manipulation means. Furthermore, this endoscope apparatus can have a compact size by winding the insertion portion on the drum portion when the endoscopy is not performed.

BRIEF DESCRIPTION OF THE DRAWINGS

FIGS. 1–11 relate to a first embodiment of the present invention, and

FIG. 1 is an explanatory diagram showing the outline construction of an endoscope apparatus of the first embodiment;

FIG. 2 is an explanatory diagram showing the outline construction of a drum portion;

FIG. 3 is a perspective view showing a tip side portion of an insertion portion;

FIG. 4 is a sectional view for explaining the construction of the tip side portion of the insertion portion;

FIG. 6 is a sectional view taken on line A—A of FIG. 4;

FIG. 7 is an explanatory diagram showing the connection state of the drum portion and a connector and the construction of an actuator section in the drum portion;

FIG. 8 is an explanatory diagram showing a concrete configuration example of the actuator section;

FIG. 9 is an explanatory diagram showing a concrete mounting example of the insertion portion and drum portion;

FIG. 10 is a block diagram for explaining the outline construction of the endoscope apparatus;

FIG. 11 is an explanatory diagram showing a curving state of the curving portion;

FIG. 12 is a sectional view of a curving portion of an endoscope apparatus having four manipulation wires and an interval maintaining wire;

FIG. 13 is an explanatory diagram showing the construction of a link mechanism constructing an actuator section;

FIG. 14 is an explanatory diagram showing the action of the link mechanism;

FIG. 15 is an explanatory diagram showing the curving state of the curving portion;

FIG. 16 is a perspective view showing a drum portion and an insertion portion in the third embodiment;

FIG. 17 is a sectional view showing the construction of a power cable-connecting portion;

FIGS. 18–22 relate to a fourth embodiment of the present invention, and

FIG. 18 an explanatory diagram showing the outline construction of an endoscope apparatus of the fourth embodiment;

FIG. 19 is a perspective view showing the construction of a drum portion;

FIG. 21 is a sectional view of a tip side of an insertion portion;

FIG. 22 is a side view showing a mounting portion of an electric curving unit in a modified example of the fourth embodiment;

FIG. 23 is a plan showing the construction of an electric curving unit with no load in the fifth embodiment;

FIG. 24 is a plan showing the electric curving unit in the neutral state of curving; and FIG. 25 is a plan showing the electric curving unit in the state of performing curving manipulation.

DESCRIPTION OF THE PREFERRED EMBODIMENTS

Figure 1:
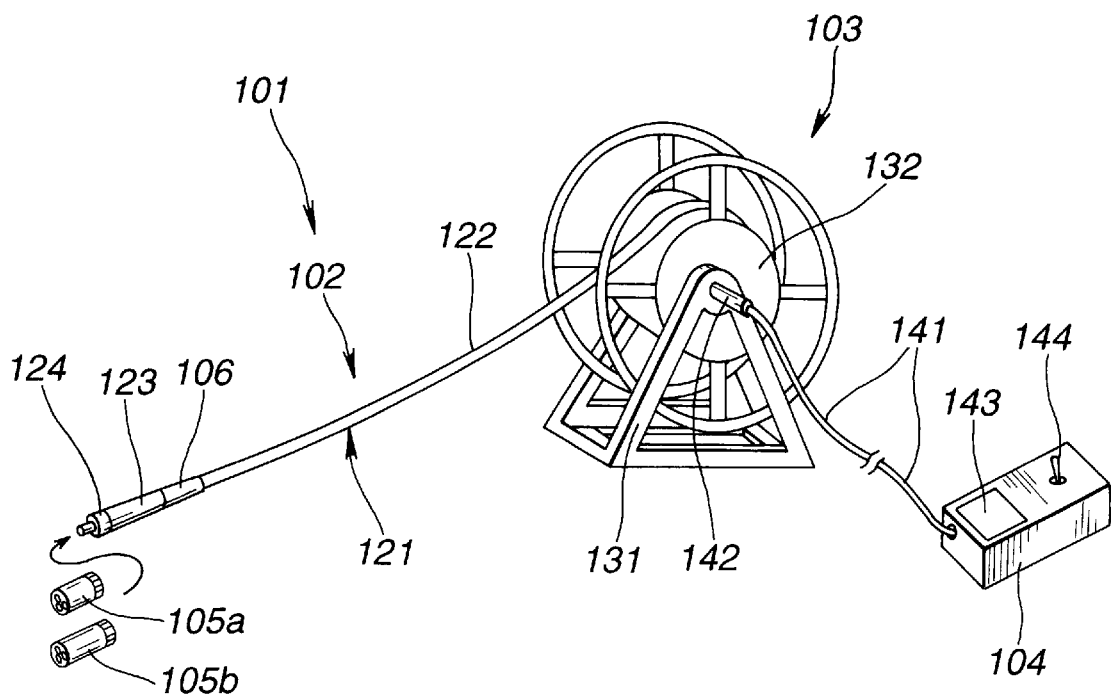

As shown in FIG. 1, an endoscope apparatus 101 according to the first embodiment is constituted of the following components. An industrial endoscope 102 has, for instance, a long, flexible insertion portion 121. A drum device 103 has a drum portion 132 that is rotatable with respect to a stand drum fulcrum 131 and on which the insertion portion 121 of the industrial endoscope (hereinafter referred to as "endoscope") 102 is wound. A controller 104 is connected to the proximal end of an elongate electric cable 141 that is detachably connected to the drum device 103. The controller 104 has a manipulation means and an observation means.

The insertion portion 121 of the endoscope 102 consists of the following components. The proximal end portion of a soft, flexible tube 122 is attached to the drum portion 132. A curving portion 123 (described later) is provided adjacent to the tip side portion of the flexible tube 122 and is so constructed as to be curved to a desired direction. A tip hard portion 124 is provided adjacent to the tip-side portion of the curving portion 123 and incorporates a solid-state imaging device as an observation optical system, such as a charge-coupled device (hereinafter abbreviated as "CCD"). The tip hard portion 124 is so constructed that plural kinds (two in FIG. 1) of tip adaptors 105a and 105b for converting the viewing angle or the viewing direction can be detachably mounted thereon. These tip adaptors 105a and 105b have different lengths, that is, different hard portion lengths.

Figure 2:
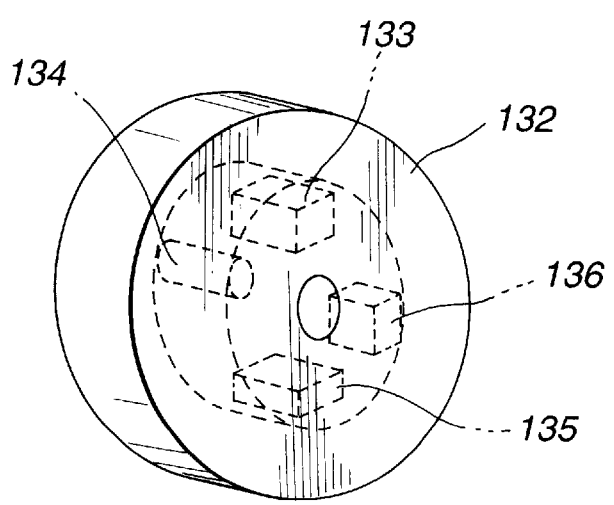

As shown in FIG. 2, the following components are provided inside the drum portion 132. A camera control unit (hereinafter abbreviated as "CCU") 133 has an image processing circuit for generating a TV signal based on an image that is picked up by the CCD, a timing generation circuit for generating timing signals for driving the CCD, and other circuits. An actuator section 134 constitutes a curving means. A control circuit 136 controls the curving state of the curving portion 123 based on an instruction signal that is sent from the controller 104. A battery 136 serves as a power supply section for the CCD, the actuator section 134, and the control circuit 135.

The CCU 133, the actuator section 134, the control circuit 135, and the battery 135 are so constructed as to be given balance weights for optimizing the weight balance of the drum portion 132 in consideration of its balance of rotation.

The tip portion of the electric cable 141 of the controller 104 is provided with a connector 142 that is detachable from a connector connecting portion (described later) provided at the rotation center of the drum portion 132. The controller 104 is also provided with a LCD monitor 143 for displaying an endoscope image that is picked up by the CCD and a joy stick 144 to be manipulated in curving the curving portion 123 to a desired direction.

The endoscope 102 will be described first.

Figure 3:
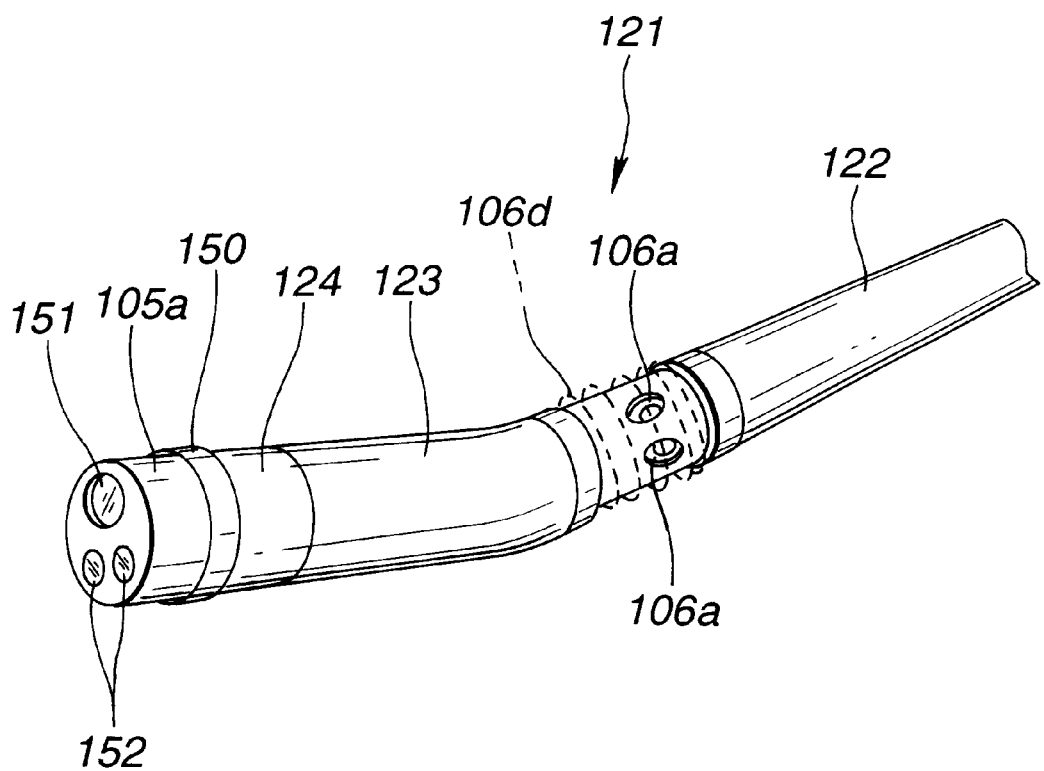

As shown in FIG. 3, for example, the tip adaptor 105a having an observation lens cover 151 that constitutes one observation window and illumination lens covers 152 that constitute two illumination windows is connected to the tip face of the tip hard portion 124. A flexible tube front connecting piece 106 is provided between the flexible tube 122 and the curving portion 123. Two metal contacts 106a are provided on the outer circumferential surface of the flexible tube front connecting piece 106.

Figure 4:
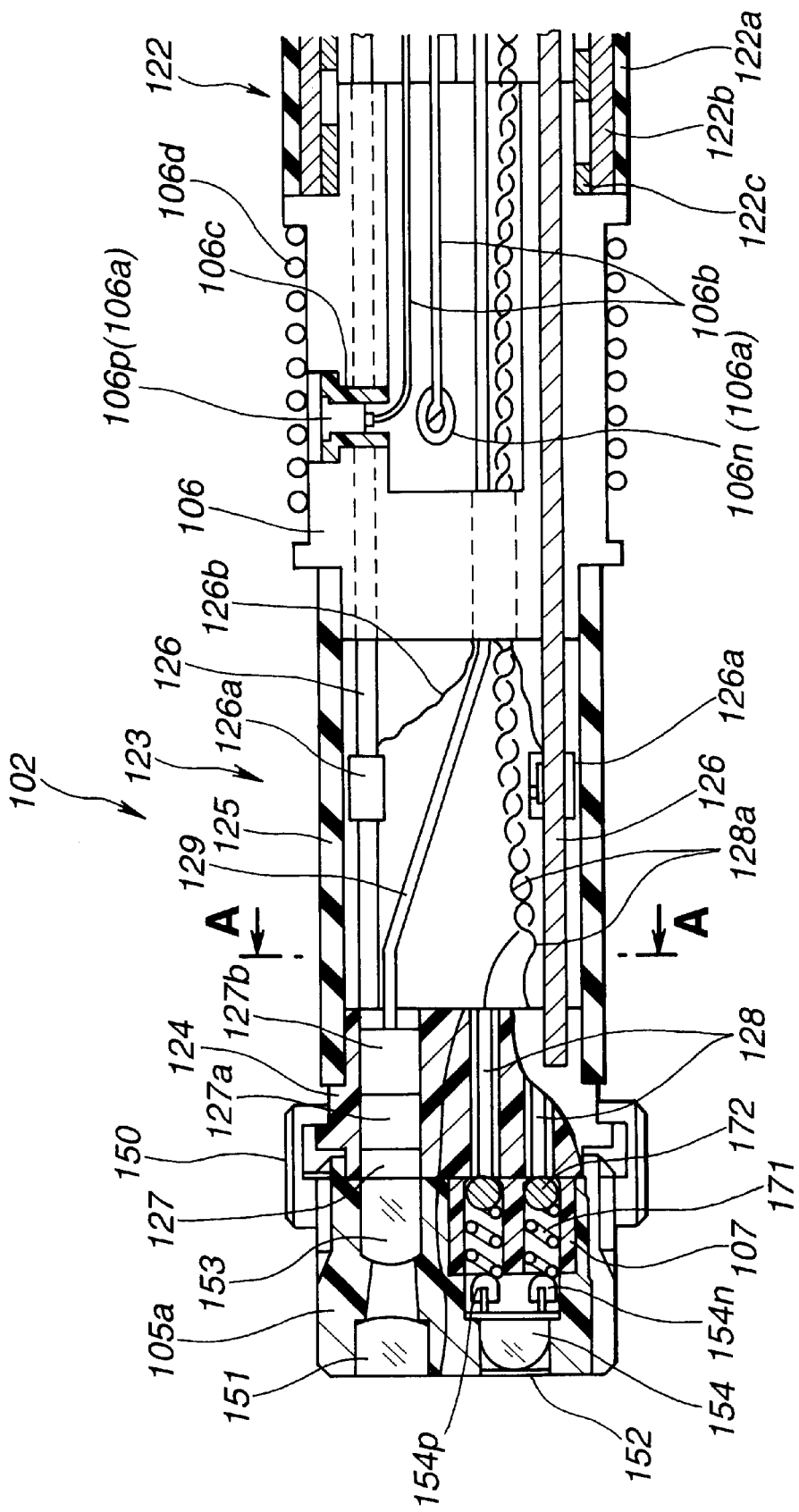

A tip-side structure of the insertion portion 121 will be described below with reference to FIG. 4.

The flexible tube 122 has a three-layer structure including, in order from the outside, an impregnated resin layer 122a, a metal mesh layer 122b, and a metal spiral tube 122c, and is thus rendered flexible.

The generally pipe-shaped flexible tube front connecting piece 106 is provided on the tip side of the flexible tube 122. The metal contacts 106a provided on the flexible tube front connecting piece 106 are a cathode metal contact 106n and an anode metal contact 106p. The metal contacts 106n and 106p are connected to the ends of electric cables 106b corresponding to the characteristics of the metal contacts 106n and 106p, respectively.

The metal contacts 106n and 106p are provided on the flexible tube front connecting piece 106 through non-conductive collars 106c. A non-conductive coil spring 106d is provided on the outer circumferential surface of the flexible tube front connecting piece 106 so as to protect the metal contacts 106n and 106p.

One end portion of a resin cover made of synthetic rubber that is an elastic member constituting the curving portion 123 covers the tip portion of the flexible tube front connecting piece 106, and the other end portion of the resin cover 125 covers the proximal end portion of the tip hard portion 124. The resin cover 125 is fixed to the flexible tube front connecting piece 106 land the tip hard portion 124 in an integral manner by means of a threadwound bonding portions (not shown) that are provided on both end portions of the resin cover 125. Thus, the resin cover 125 bridges the flexible tube front connecting piece 106 and the tip hard portion 124 with a given space provided in between. Instead of the resin cover 125, a tubular elastic member made of a material that is high in both flexibility and straight extendability, such as a super elastic alloy (Ni—Ti alloy), may be used.

One end portions of manipulation wires 126 as wire members that constitute, together with the resin cover 125, the curving portion 123 are connected to the tip hard portion 124. The manipulation wires 126 are wire members made of a Ni—Ti type alloy that exhibits a super elastic characteristic and is generally called a super elastic alloy. The manipulation wires 126 extend through the flexible tube front connecting piece 106 and the flexible tube 122, and the other end portions of the manipulation wires 126 are connected and fixed to the actuator section 134 as the curving means for moving the manipulation wire 126 in the longitudinal direction of the insertion portion 121. The actuator section 134 is provided in the drum portion 132. In the third embodiment, three manipulation wires 126 are used, an arrangement of which will be described later with reference to FIG. 6.

To detect a curving direction, each of the manipulation wires 126 is provided, in the curving portion 123, with a sensor 126a such as a strain gauge. Curving state detection signals produced by the respective sensors 126a are transmitted by signal transmission lines 126b extending from the respective sensors 126a and input to the control circuit 135 in the drum portion 132.

The tip hard portion 124 is provided with a CCD 127 that constitutes an observation optical system and contact electrodes 128 as second electrical contacts to serve as cathode and anode contacts for supplying illumination power to, for instance, an LED device (hereinafter referred to as "LED") as a light-emitting element that constitutes an illumination optical system (described later).

The CCD 127 has a driver circuit 127a for driving it, a preamplifier 127b for amplifying an electrical signal produced through photoelectric conversion of an image formed on the imaging surface of the CCD 127, and other circuits. A signal cable 129 for signal exchange extends from the driver circuit 127a and the preamplifier 127b to the drum portion 132, going through the flexible tube front connecting piece 106 and the flexible tube 122. The proximal end of the signal cable 129 is connected to the CCU 133 that is provided in the drum portion 132.

On the other hand, one end of electric wires 128a corresponding to the characteristics of the above-mentioned contact electrodes 128 are connected to those electrodes, respectively. The electric wires 128a goes through the insertion portions 121 and the other ends of electric wires 128a are connected to the battery 136 which is provided in the drum portion 132.

The tip portion of the tip hard portion 124 is provided with the tip adaptor 105a having an observation lens cover 151 and an objective lens 153 that constitute the observation optical system and an LED 154 that emits illumination light. The tip adaptor 105a is connected and fixed to the tip of the insertion portion 121 through a rotary ring 150 whose inner circumferential surface is formed with a female thread portion that engages a male thread portion (not show) formed on the outer circumferential surface of the tip hard portion 124.

The rotary ring 150 is provided with a water-tight member (not show) for preventing dust, water, or the like from entering the inside of the endoscope 102 through the connecting portion of the tip adaptor 105a and the tip hard portion 124.

The LED 154 which is provided in the tip adaptor 105a has a cathode teminal 154n and an anode teminal 154p that are opposed to the contact electrodes 128 provided in the tip hard portion 124. The optical axis of the LED 154 coincides with the viewing direction of the observation optical system.

Figure 5A:
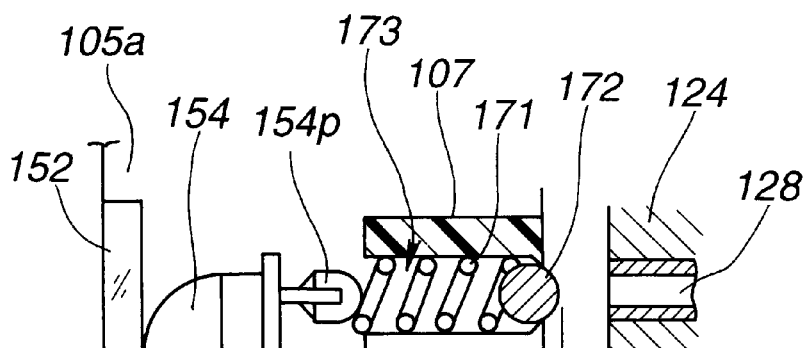
FIGS. 5a and 5b are diagrams for explaining the construction and action of a conductive holder provided in a tip adaptor.

The tip adaptor 105a is provided with a conduction holder 107 that is made of an insulativematerial. The conduction holder 107 is formed with fitting through-holes 173 which are fitted with conductive, coil-shaped compression springs 171 and metal balls 172 for electrical conduction between the contact electrodes 128 and the cathode and anode terminals 154n and 154p of the LED 154. As show in FIG. 5a, when the fitting through-holes 173 are fitted with the metal balls 172 and the compression springs 171, the cathode and anode terminals 154n and 154p contact the end faces of the respective compression springs 171. Thus, first electrical contacts are formed.

In a state that the tip adaptor 105a is not attached to the tip hard portion 124, urging force of the compression strings 171 causes the balls 172 (provided on the proximal side) to project from the proximal face by a dimension a.

Figure 5B:
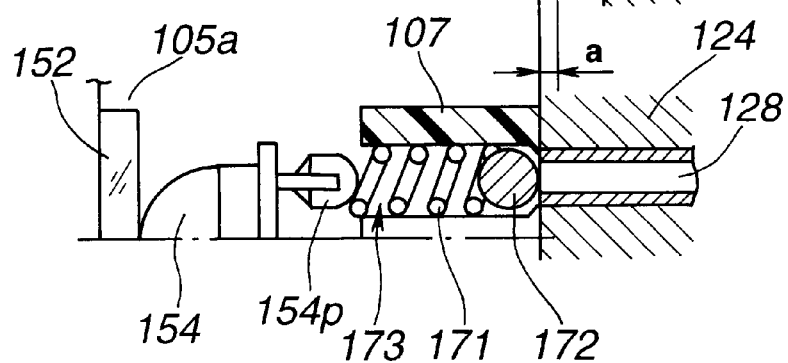

On the other hand, as show in FIG. 5b, in a state that the tip adaptor 105a is attached to the tip hard portion 124, the metal balls 172 being urged by the compression springs 171 are brought in contact with the tip faces of the respective contact electrodes 128.

As a result, the LED 154 is turned on being supplied with illumination power from the battery 136 via the electric wires 128a, the contact electrodes 128, the metal balls 172, the compression springs 171, and the cathode and anode terminals 154n and 154p. Since the urging force of the compression springs 171 causes the metal balls 172 to be always pressed against the tip faces of the respective contact electrodes 128, reliable conduction can be obtained irrespective of the manipulation on the endoscope 102.

Figure 6:
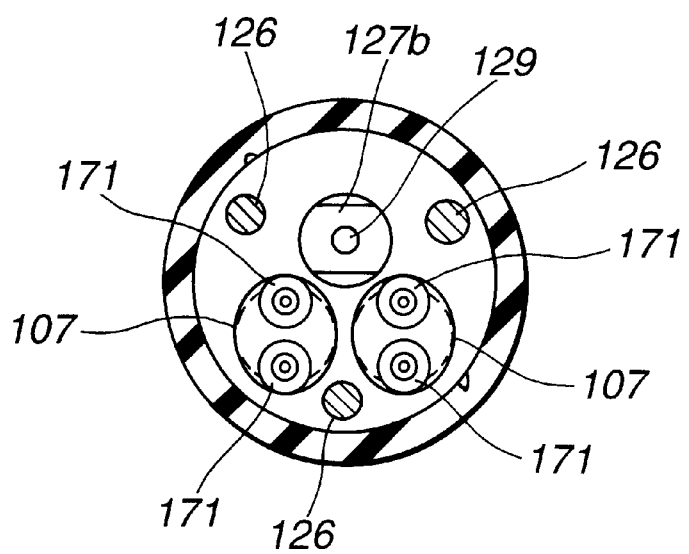

As shown in FIG. 6, the three manipulation wires 126 which are part of the curving portion 123 are provided in equilateral triangle form and fixed to the tip hard portion 124 at positions close to its outer circumferential surface to secure sufficient internal space, so as not to butt against the contact electrodes 128 for supplying power to the LED 154.

The three manipulation wires 126, which are fixed to the tip hard portion 124 and extend to the drum portion 132, are arranged such that at least one of a plurality Of planes each formed by an arbitrary pair of the three manipulation wires 126 does not include the central axis of the insertion portion 121(curving portion).

Therefore, when at least one of the three manipulation wires 126 is moved by the actuator section 134, the remaining manipulation wire(s) 126 that is not moved by the actuator section 134 resists the moving manipulation wire 126 and is curved toward the moving manipulation wire 126.

Next, the drum device 103 will be described.

Figure 7:
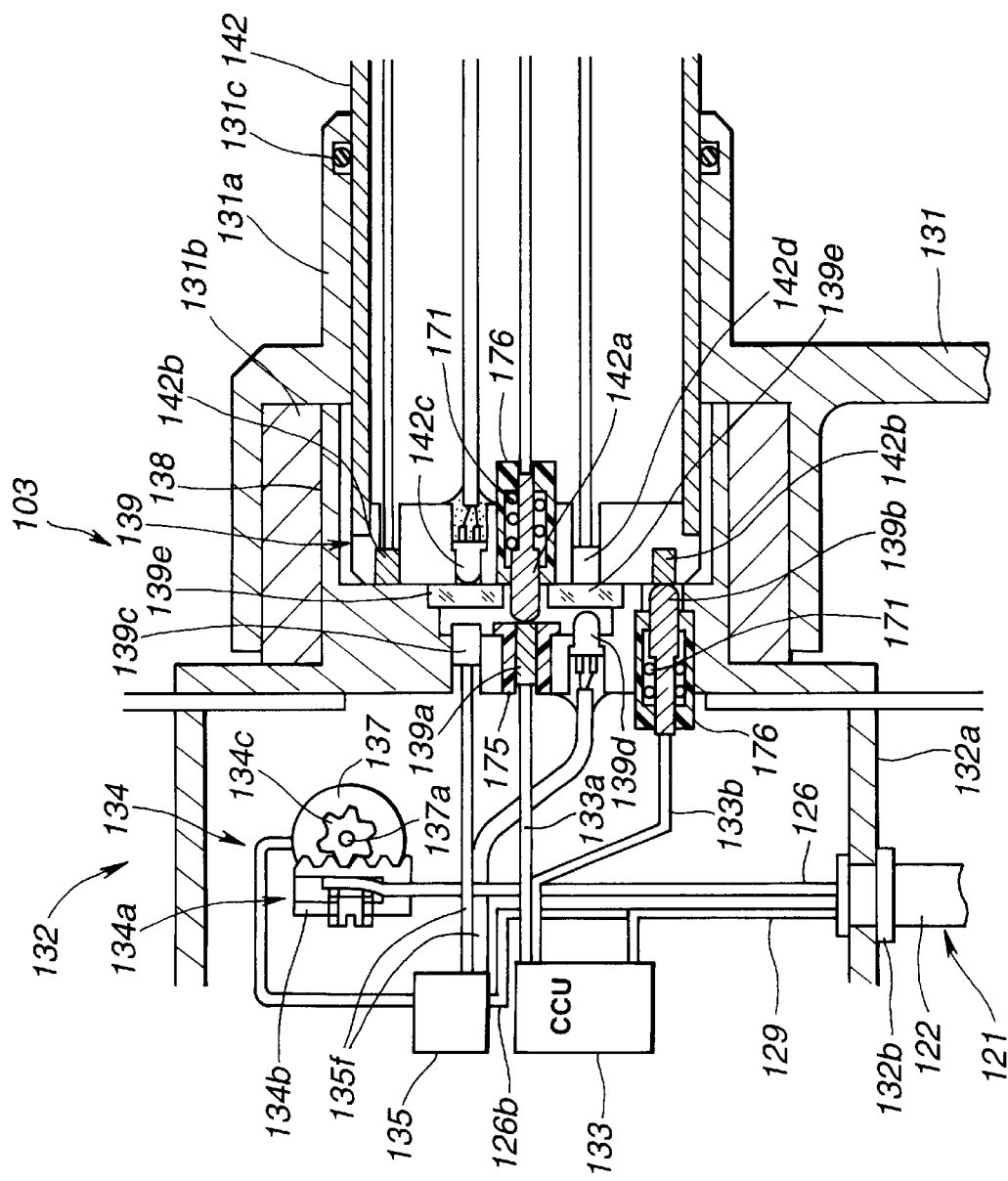

As shown in FIG. 7, the proximal end portion of the flexible tube 122 which is part of the insertion portion 121 is connected to a connection member 132b that is provided on a winding surface 132a of the drum portion 132. Each of the manipulation wires 126 goes through the curving portion 123, the flexible tube front connecting piece 106, and the flexible tube 122, and reaches the inside of the drum portion 132. One end portion of each manipulation wire 126 is connected to a rack 134b a rack-pinion portion 134a that constitutes the actuator 134.

The rack 134b advances or retreats in accordance with the rotation of a pinion 134c, which is rotated by a motor 137. The motor 137 is fixed to the inside of the drum portion 132.

Figure 8:
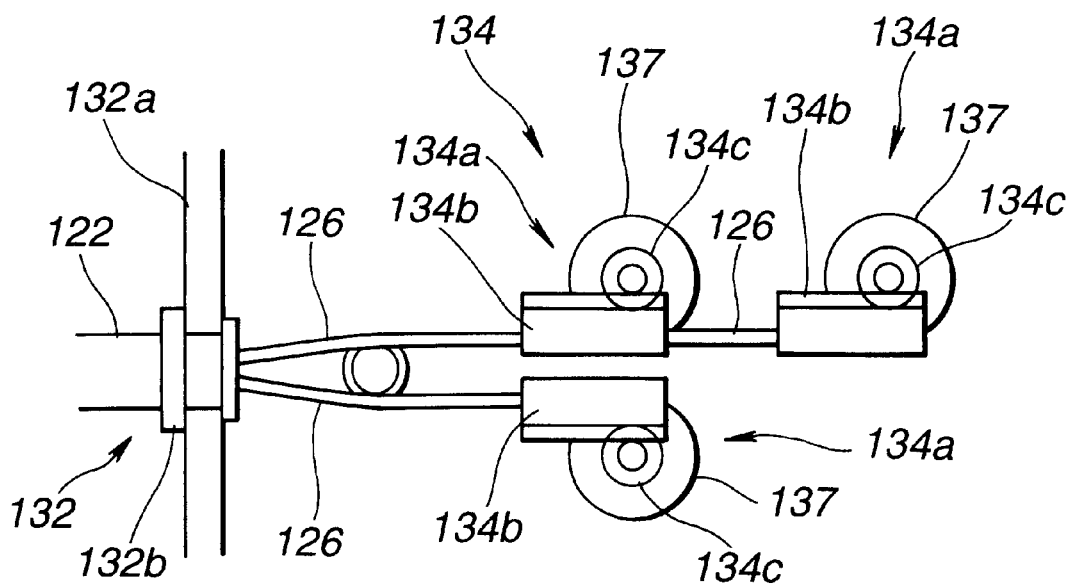

As shown in FIG. 8, three rack-pinion portions 134a are provided in the actuator section 134 so as to correspond to the three respective manipulation wires 126 which are inserted in the insertion portion 121. The end portion of each manipulation wire 126 is connected to the rack 134b of each rack-pinion portion 134a.

The manipulation wires 126 advance or retreat independently of each other in accordance with the operations of the respective rack-pinion portions 134a. By causing the respective rack-pinion portions 134a to advance or retreat by properly controlling their operations, the manipulation wires 126 that are fixed to the respective racks 134b advance or retract accordingly, whereby the curving portion 123 is curved to a desired direction.

An alternative configuration is possible in which the curving portion 123 is curved by pushing at least one of the manipulation wires 126 from the initial position where a curve is canceled to the curving portion side, and the curve thus produced is canceled by returning the manipulation wire 126 to the initial position.

As shown in FIG. 7, the end portions of the signal transmission lines 126*b* and the signal cable 129 that go through the insertion portion 121 and reach the inside of the drum portion 132 are connected to the control circuit 135 and the CCU 133, respectively, which are provided in the drum portion 132.

Figure 9:
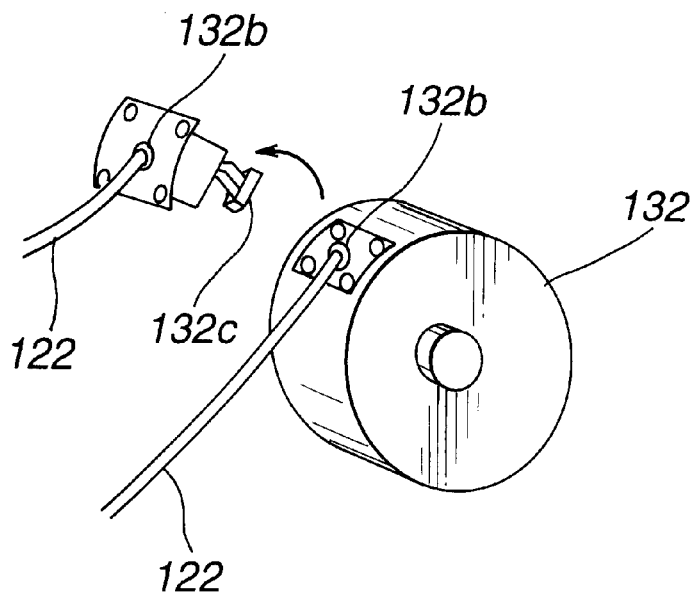

As for a specific manner of attaching the insertion portion 121 of the endoscope 102 to the drum portion 132, reference is made to FIG. 9. That is, as show in FIG. 9, the connection member 132*b* to which the proximal end portion of the flexible tube 122 (insertion portion 121) is connected can be detachably fixed to the winding surface 132*a* of the drum portion 132 with vises.

The connection member 132*b* is provided with a connector 132*c* that is electrically connected to the CCU 133 and the control circuit 135 (and the battery 136) which are provided in the drum portion 132. By connecting the connector 132*c* of the connection member 132*b* to a corresponding connector in the drum portion 132, the signal transmission lines 126*b* and the signal cable 129 which are inserted in the insertion portion 121 are connected to the control circuit 135 and the CCU 133.

The connection between the insertion portion 121 and the drum portion 132 is completed by fixing the connection member 132*b* to the winding surface 132*a* with vises after the connector 132*c* is connected to the corresponding connector.

To obtain a rotation speed that is reduced from the rotation speed of the motor 137, a reduction gear mechanism may be provided between a rotary shaft 137*a* of the motor 137 and the pinion 134*c*.

Next, a description will be made of a connection relationship between the controller 104 and the control circuit 135 and the CCU 133.

As shown in FIG. 7, a connector receptacle 131*a* incorporating a bearing portion 131*b* projects from a side face of the stand 131 of the drum device 103. A shaft portion 138, which projects from a side face central portion of the drum portion 132 and has a plurality of contact portions on the bottom face of a connector connecting portion 139, is attached to the bearing portion 131*b* of the connector receptacle 131*a* so as to be rotatable with respect to the stand 131.

The bottom face of the connector connecting portion 139 of the shaft portion 138 which projects from the drum portion 132 is provided with a video signal contact electrode 139*a* to which a video signal line 133*a* extending from the CCU 133 is connected and a ground (or GND) teminal 139*b* to which a ground line 133*b* is connected, as veil as with communication photodiodes 139*c* and communication LEDs 139*d* that are connected to communication cables 135*f* for bidirectional communication extending from the control circuit 135.

The video signal contact electrode 139*a* to which the video signal line 133*a* is connected is provided in a non-conductive first holder 175 that is located on the rotation central axis of the drum portion 132.

On the other hand, the GND teminal 139*b* to which the ground line 133*b* is connected is accommodated in a non-conductive second holder 176 that is located at a position distant from the video signal contact electrode 139*a* and close to the outer circumferential surface of the connector connecting portion 139. The GND teminal 139*b* is always urged sideways and outward by a compression spring 171 that is provided in the second holder 176. Diffusion plates 139*e* are disposed in front of the communication photodiodes 139*c* and the communication LEDs 139*d*.

On the other hand, the tip face-of a connector 142 that is inserted in the connector receptacle 131*a* and connected to the connector connecting portion 139 is provided with a video signal connection teminal 142*a*, a GND contact electrode 142*b*, communication LEDs 142*c*, and communication photodiodes 142*d* so as to be opposed respectively to the video signal contact electrode 139*a*, the GND teminal 139*b*, the diffusion plates 139*c* that are disposed in front of the communication photodiodes 139*c* and the communication LEDs 139*d*.

The video signal connection teminal 142*a* is accommodated in a non-conductive third holder 176*a* that is sealed and fixed with a filler or the like at the center of the connector 142. The video signal connection teminal 142*a* is always urged sideways and outward by a compression spring 171*a* that is provided in the third holder 176*a*.

The communication LEDs 142*c* and communication photodiodes 142*d* are sealed and fixed with a filler or the like so as to be opposed respectively to the communication photodiodes 139*c* and the communication LEDs 139*d* which are provided in the connector connecting portion 139. Further, the GND contact electrode 142*b* is formed in ring-like form the tip face of the connector 142 so as to provide reliable conduction with the GND teminal 139*b* which is located close to the outer circumferential surface of the connector connecting portion 139.

With the above configuration, light that is emitted from the communication LEDs 142*c* based on a curving instruction signal that is produced as a result of a manipulation on the joy stick 144 provided on the controller 104 is diffused by the diffusion plates 139*e* of the connector connecting portion 139, reaches the photodiodes 139*c*, and finally transmitted to the control circuit 135 via the communication cable 135*f*.

Even if the connector 142 is attached to the connector connecting portion 139 in any circumferential positional relationship with the latter, emitted light is transmitted, as a curving instruction signal, to the control circuit 135 in a reliable manner by Virtue of the use of a plurality of communication LEDs 142*c* and the diffusion effect of the diffusion plates 139*e*.

Since the video signal connection teminal 142*a* to contact the video signal contact electrode 139*a* which is connected to the video signal line 133*a* extending from the CCU 133 and the GND teminal 139*b* to contact the GND contact electrode 142*b* provided in the connector 142 are always pressed by the urging force of the compression springs 171*a* and 171 to as to contact the contact electrodes 139*a* and 142*b*, respectively, signal exchange can be performed in such a state that reliable conduction is established between the terminals 139*b* and 142*a* and the contact electrodes 139*a* and 142*b*.

An O-ring 131*c* is provided on the inner circumferential surface of the connector receptacle 131*a* on its mouth side to prevent entrance of dust, water, or the like into the inside of the connecting portion as well as falling of the connector 142 from the connector receptacle 131*a*.

Figure 10:
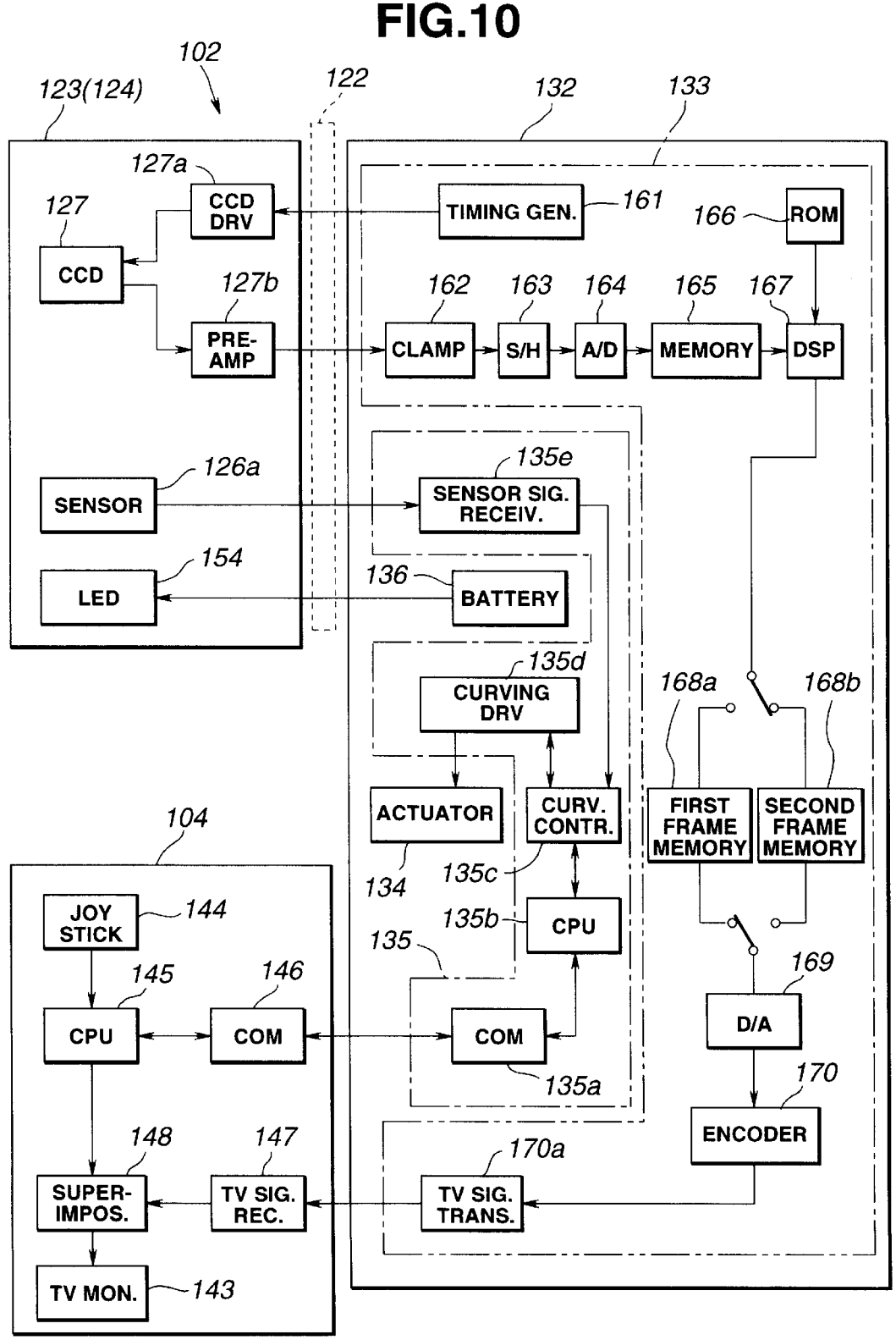

The operation of the above-configured endoscope apparatus 101 will be described with reference to a block diagram of FIG. 10.

The tip hard portion 124 of the endoscope 102 is provided with the LED 154 for illuminating a part to be observed, the CCD 127 for imaging the part to be observed that is illuminated by the LED 154, the driver circuit 127a for driving the CCD 127, and the preamplifier 127b for amplifying an electrical signal that is produced through photoelectric conversion of an image formed on the imaging surface of the CCD 127.

The sensors 126a for detecting curving states of the respective manipulation wires 126 are provided at intermediate positions, in the curving portion 123 of the manipulation wires 126 whose tips are fixed to the tip hard portion 124 and which extend to the actuator section 134.

The drum portion 132 of the drum device 103 incorporates the CCU 133 having the image processing circuit for producing a video signal from an electrical signal supplied from the CCD 127 and other circuits, the actuator section 134 for advancing or retreating the manipulation wires 126, the control circuit 135 for controlling, for instance, a curving state of the curving portion 123, and the battery 136 as a power supply.

The LED 154 is turned on being supplied with power from the battery 136 when the flexible tube 122 constituting the insertion portion 121 is connected and fixed to the drum portion 132.

The controller 104 is provided with the joy stick 144 as a manipulation switch, A CPU 145 for converting a movement of the joy stick 144 into a curving instruction signal, a communication circuit 146 for supplying the thus-produced curving instruction signal to the control circuit 135, a TV signal receiving circuit 147 as a receiving section of a TV signal that is transmitted from the CCU 133, the LCD monitor 143 as a TV monitor, and a superimposer 148 for causing the LCD monitor 143 to display image information and text information.

The CCD driver circuit 127a which is provided in the tip hard portion 124 is driven by drive signals that are output from a timing generation circuit 161 that is provided in the CCU 133.

An electrical signal obtained by amplification, by the preamplifier 127b, of a signal that is produced based on an image formed on the imaging surface of the CCD 127 is transmitted to an image processing circuit of the CCU 133. In the image processing circuit, the received electrical signal is subjected to known processing in the clamping circuit 162 and a sample hold circuit 163, amplified by a amplifier (not shown), and then A/D-converted by an A/D conversion circuit 164.

Image data produced by the A/D conversion is input to a memory 165. Based on the image data, a DSP (digital signal processor) 167 produces a video signal of a given format according to a program stored in a DSP ROM 166. After passing through a first frame memory 168a or a second frame memory 168b, the video signal is D/A-converted by a D/A conversion circuit 169 and then input to an encoder 170, which produces a TV signal to be output to the external apparatus. The TV signal is output to the TV signal receiving circuit 147 of the controller 104 via a TV signal transmission circuit 170a.

In summary, an image that is picked up by the CCD 127 is converted into an electrical signal, which is amplified by the preamplifier 127b and then transmitted to the CCU 133. Based on the received electrical signal, the CCU 133 produces a TV signal, which is output to the TV signal receiving circuit 147 of the controller 104 via the TV signal transmission circuit 170a. The TV signal is then displayed on the LCD monitor 143 via the superimposer 148.

When a curving manipulation on the curving portion 123 is made by manipulating the joy stick 144 of the controller 104, a curving instruction signal representing a movement of the joy stick 144 is supplied from the joy stick 144 to a control CPU 135b via the CPU 145, the communication circuit 146, and a communication circuit 135a of the control circuit 135 which is provided in the drum portion 132.

Upon reception of the curving instruction signal, the control CPU 135b controls, via a curving control circuit 135c, a curving driver circuit 135d so that the curving driver circuit 135d supplies a drive signal to a related motor 137 of the actuator section 134, to start driving the motor 137. As a result, the pinion 134c is rotated by a specified amount in a specified direction, the rack 134b is moved accordingly, and finally the corresponding manipulation wire 126 is moved in the specified direction.

Figure 11:
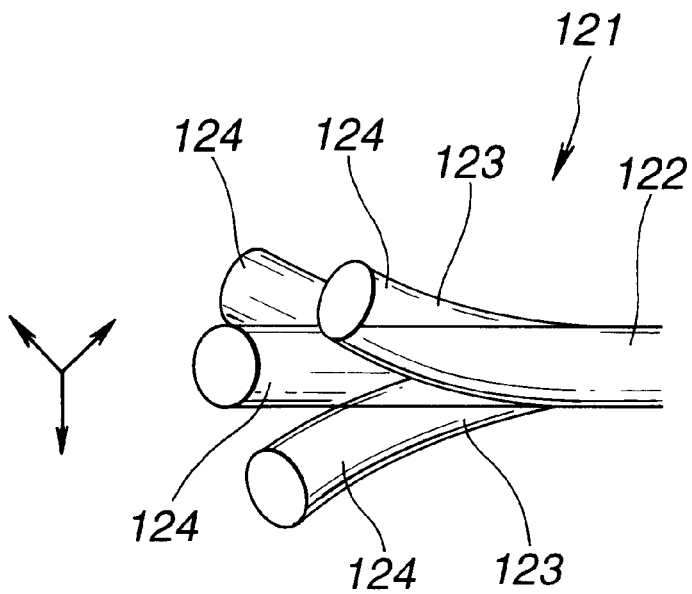

As a result, the remaining, i.e., unmoved, manipulation wire(s) 126 resists the moving manipulation wire 126, to establish a state that the tip hard portion 124 is pulled toward the flexible tube front connecting piece 106. Thus, the manipulation wires 126 are warped and the curving portion 123 is curved to one of the directions indicated by arrows in FIG. 11.

When the curving portion 123 starts to curve as show in FIG. 28, stress amounts are detected by the sensors 126a which are provided on the respective manipulation wires 126, and curving state detection signals representing the respective stress amounts are transmitted to a sensor signal receiving circuit 135e of the control circuit 135.

The received curving state detection signals are supplied to the control CPU 135b via the curving control circuit 135c. After the curving state detection signals are compared with the curving instruction signal that is supplied from the joy stick 144, the curving driver circuit 135d again outputs a drive signal to the actuator section 134, which advances or retreats the respective manipulation wires 126 so that the curving portion 123 is curved in the direction according to the instruction from the joy stick 144.

As described above, where the distal end portion of the three manipulation wires 126 each made of a super elastic alloy are fixed to the tip hard portion 124 which is located at the tip of the insertion portion 121, the three manipulation wires 126 are arranged so that at least one of planes each of which is formed by arbitrarily selected two of the three manipulation wires 126 does not include the central axis of the tip hard portion 124 and the curving portion 123 which constitute the insertion portion 121, and the curving mechanism is constructed by connecting the proximal ends of the respective manipulation wires 126 to the rack-pinion portions 134a which advance or retreat the respective manipulation wires 126. Thus, by properly adjusting the movements of the respective manipulation wires 126 for the respective rack-pinion portions 134a, the curving portion 123 can be curved to a desired direction.

The sensors 126a for detecting curving states of the three respective manipulation wires 126 are provided thereon at the intermediate positions, in the curving portion 123, of the respective manipulation wires 126, and curving state detection signals that are output from the respective sensors 126a are supplied to the curving control circuit 135c of the control circuit 135. The curving state detection signals are compared with a curving instruction signal that is supplied from the joy stick 144. Based on comparison results, a drive signal for controlling the curving state of the curving portion 123 is newly output to the actuator section 134 from the curving driver circuit 135d, to advance or retreat the respective manipulation wires 126. Thus, the curving portion 123 can be curved in a reliable manner to the direction according to the instruction from the joy stick 144.

Further, by virtue of the fact that the curving portion 123 and the curving mechanism are formed by using the three manipulation wires 126, wider space can be secured in the curving section 123 than in the conventional curving portion that is constituted of a plurality of curving blocks and a manipulation wire for curving a curving tube that is formed by the plurality of curving blocks. Since sufficient space for insertion of the internal components other than the curving mechanism is secured, it is no longer necessary to reduce the diameters of the respective internal components and, on the other hand, it becomes possible to reduce the diameter of the endoscope insertion portion.

The LED 154 is provided in the tip adaptor (105a), and illumination light is emitted from the LED 154 that is supplied with power from the battery 136 of the drum portion 132 when the flexible tube that constitutes the proximal portion of the insertion portion 121 is connected to the drum portion 132. In this manner, a part to be inspected can always be illuminated with a necessary amount of light.

By virtue of the fact that the video signal contact electrode 139a to which the video signal line 133a extending from the CCU 133 is connected and the video signal connection terminal 142a which is provided in the connector 142 are located on the rotation central axis of the drum portion 132, a failure in conduction between the video signal contact electrode 139a and the video signal connection teminal 142a due to the rotation of the drum portion 132 can be prevented in a reliable manner.

Further, the metal balls 172 which are provided in the tip adaptor (105a) are always pressed against the tip faces of the contact electrodes 128 by the urging force of the compression springs 171, and the video signal connection teminal 142a and the ground teminal 139b are always pressed against the video signal contact electrode 139a and the ground contact electrode 142b by the urging force of the compression springs 171a and, 171, respectively. Therefore, reliable conduction can be established between the metal balls 172 and the contact electrodes 128, between the video signal connection teminal 142a and the video signal contact electrode 139a, and between the ground teminal 139b and the ground contact electrode 142b.

Although in the first embodiment the LED 154 is used as the illumination means, a similar configuration may be obtained by replacing the LED 154 with a lamp.

In addition, this embodiment has also the following effects.

Since curving manipulation means performing curving manipulation and curving drive means making the curving portion curve through manipulation wires (wires for curving) by this curving manipulation are separated and the curving drive means is located inside the drum portion, it becomes easy to wind up and contain the insertion portion and it becomes possible at the same time to compactly contain the entire insertion portion.

In addition, since it is possible to locate the curving manipulation means outside the drum portion freely movably, a user can perform the curving manipulation at an easy-manipulation place.

Furthermore, since it becomes possible to connect manipulation wires led out of the insertion portion in a shortest distance and simple construction to the curving drive means in the drum portion, it is possible to effectively transmit a driving force to the manipulation wires.

Against this, in consideration of a case that the curving drive portion is provided outside the drum portion separately from the insertion portion, it becomes necessary to perform back-and-forth manipulation of the manipulation wires through the rotating drum. Nevertheless, a technical barrier to realize that is extremely high, and even if it is realized, size, weight, cost, reliability, energy loss of wire drive, and the like are extremely large in comparison to the construction of this embodiment.

Therefore, this embodiment has also an advantage at this point. In addition, since the curving manipulation is performed with only the back-and-forth manipulation of manipulation wires inserted into the insertion portion, it is possible to suppress the size of a curving mechanism in the insertion portion at the minimum. Owing to this, it becomes possible to make the outer diameter of the insertion portion small.

Furthermore, the curving portion can comprise a flexible, pipe-shaped member having a function of a sheathing tube, and a plurality of manipulation wires located eccentrically to the center axis of this pipe-shaped member. Therefore, it is possible in this embodiment to make the curving portion sufficiently slender, the curving portion which is a part where the outer diameter of the insertion portion easily becomes large.

In addition, since the U.S. Pat. No. 5,090,259 has a construction of performing the curving by locating the rubber artificial muscles on the outer circumferential surface of the insertion portion, the tip portion of the insertion portion becomes large, and hence the range of objects where the insertion portion can be inserted and inspected are restricted.

Moreover, since in U.S. Pat. No. 5,373,317 a curving input control portion and a drive portion by electric motors are unified, it is not possible to overcome a task of compactly containing the entire insertion portion with achieving excellent property of containment.

Furthermore, in U.S. Pat. No. 4,941,456, it is never referred to achieve the excellent property of containment by winding up and locating an insertion portion on a drum.

In addition, in Japanese Patent Publication No. 5-56486, it is not shown to improve the property of containment by winding up an object, including an endoscope system having a curving mechanism, on a drum.

Moreover, Japanese Unexamined Patent Publication No. 4-81711 (hereinafter, Takehana's Patent) discloses the construction of separating a drive portion generating mechanical energy from a curving input control portion and winding up and locating an insertion portion on a drum. Nevertheless, it produces a severe defect on compactness of the entire system to locate outside the drum the means for generating the mechanical energy (a compressor or a compressed air cylinder) because the means has a size to some extent. When the insertion portion is wound up and located, it is not possible to infinitely minimize a diameter of winding because it is necessary to avoid an obstruction to functions of the insertion portion. Therefore, Takehana's Patent is distinguished from the present invention pursuing compactness of the system, because a space is not used effectively, the space which is secured in an inner circumferential surface of the drum on which the insertion portion is wound up and located, that is, inside the drum.

Furthermore, it is a very important element for realizing the excellent curving performance in a limited space to efficiently transmit the mechanical energy to the curving portion.

Tanehana's Patent bears a conclusive handicap that the mechanical energy should be transmitted to the insertion portion through a rotating drum because the drive portion is located outside the drum. (That is heavy load that cannot bear compared with a case that electrical energy is transmitted through a rotor, which is established and generates few loss.) Compensation to be paid, such as size, weight, cost, reliability, and energy loss is extremely large. Also in this point, the thought of invention of Takehana's Patent is incompatible with the advancing thought of invention of the present invention.

Furthermore, since this embodiment does not drive the manipulation wires manually but drives them with electric drive means, a user can instruct a curving direction only with a joy stick and the like. Hence, the user can easily make the curving portion curve to a desired direction, and hence it is possible to realize a good curving manipulability.

Assuming that the curving portion is made manually to curve, it becomes necessary to widely move a curving knob when the curving manipulation is performed since the insertion portion of the endoscope apparatus for industrial use is very long and hence play of the manipulation wires is also long. Furthermore, it also becomes necessary to strengthen the curving force far more than the case that a short insertion portion like an endoscope apparatus for medical use is used. Therefore, the electric drive means like that in this embodiment is desirable.

In addition, since in this embodiment the electric curving drive means and a CCU are contained in the drum portion, it is possible to realize an endoscope apparatus that a battery in the drum portion can commonly supply a power supply voltage to and is more compact.

Furthermore, although a motor constructing the curving drive means easily becomes a source generating radiation noise, it becomes possible to reduce the noise radiated to the outside of a housing with the conductive housing of the curving drive means by containing the curving drive means in the drum portion. Moreover, it becomes possible to reduce the radiation noise to the outside of the drum portion by forming the drum portion with a conductive member.

In addition, since it becomes possible to take an EMC measure in a housing by containing the curving drive means and CCU in the conductive housing, it becomes to make an endoscope apparatus more compact than that having separate housings.

FIGS. 12–15 relate to a second embodiment of the invention.

The configuration of an endoscope 102 will be described first.

Figure 12:
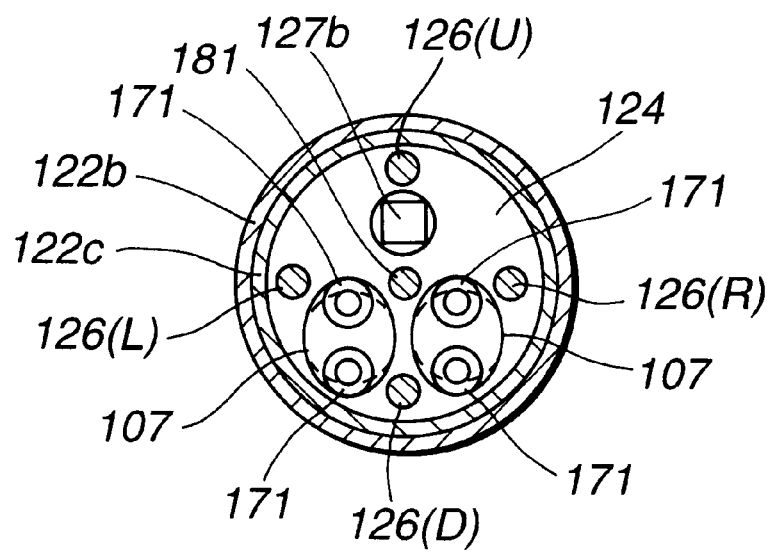
FIGS. 12–15 relate to a second embodiment of the present invention.

As shown in FIG. 12, in the second embodiment, four manipulation wires 126 are used, that is, the number of manipulation wires 126 is increased by one from the case of the first embodiment. The four manipulation wires 126 are fixed to the tip hard portion 124 at four equally divided positions close to its outer circumferential surface so as to serve as up, down, right, and left manipulation wires 126U, 126D, 126R, and 126L.

One end of an interval maintaining wire 181 as a wire rod for keeping the interval of the curving portion 123 at a given value is fixed to the tip hard portion 124 at a position approximately on the central axis. The other end of the interval maintaining wire 181 is fixed to the flexible tube front connecting piece 106 at a position approximately on the central axis.

Further, the resin cover 125 which covers the curving portion 123 in the third embodiment is replaced by a composite tube of a metal mesh tube 122b and a metal spiral tube 122c that are provided concentrically. In the composite tube, either the metal mesh tube 122b or the metal spiral tube 122c may be provided outside.

Next, the structure of an actuator section 134 will be described.

Figure 13:
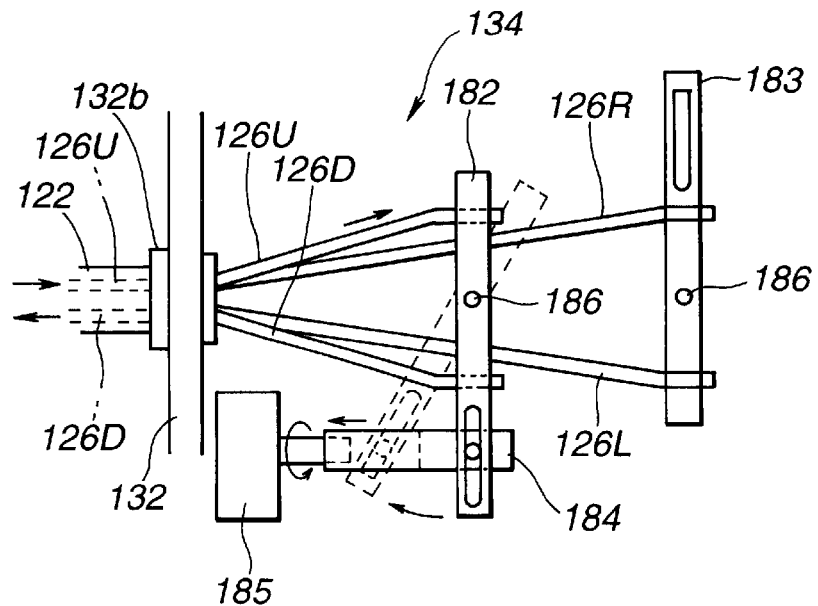

As shown in FIG. 13, the actuator section 134 of the fourth embodiment is constituted of a link mechanism portion having a top/bottom link bar 182 to which the up and don manipulation wires 126U and 126D are connected and a right/left bar 183 to which the right and left manipulation wires 126R and 126L are connected, screw-type linear driving members 184 that are respectively connected to the up/don link bar 182 and the right/left link bar 183, motors 185 for driving the respective screw-type linear driving members 184. In FIG. 13, the screw-type linear driving member 184 connected to the right/left link bar 183 and the motor 185 for driving it are omitted.

Figure 14:
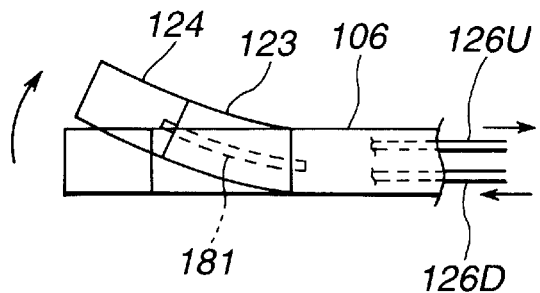

The link bar 182 which constitutes a up/down link mechanism portion is axially supported so as to be rotatable about a shaft 186 that is fixed to the inside of the drum portion 132. One end of the link bar 182 is connected to one end of the screw-type linear driving member 184 which is advanced or retreated by the motor 185. With this structure, for example, by rotating the motor 185 by a drive signal that is supplied from the curving driver circuit 135d, the link bar 182 which is connected to the screw-type linear driving member 184 from a position indicated by solid lines to a position indicated by broken lines. As a result, as shown in FIG. 14, the up manipulation wire 126U is pulled while the down manipulation wire 126D is pushed; that is, a pair of manipulation wires 126U and 126D are simultaneously subjected to a push/pull manipulation. As a result, the curving portion 123 is curved to the direction of the up manipulation wire 126U that is being pulled.

The structure relating to the right-left direction is not described because it is the same as the above-described structure relating to the up-down direction. The up and down manipulation wires 126U and 126D are fixed to the link bar 182 at positions that are equally distant from the shaft 186 as the supporting point. Similarly, the right and left manipulation wires 126R and 126L are fixed to the link bar 183 at positions equally distant from the shaft 186. Since the other structures of the first embodiment are the same as those of the first embodiment, descriptions therefor are omitted with the same parts and components given the same reference symbols.

Next, the operation of the above-configured endoscope apparatus will be described.

As in the case of the first embodiment, a curving instruction signal is supplied to the control CPU 135b by manipulating the joy stick 144. In response, the control CPU 135b controls, via the curving control circuit 135c, the curving driver circuit 135d so that the curving control circuit 135d supplies drive signals to the motors 185 corresponding to the up/don and right/left directions, respectively, whereby the motors 185 start rotating. As a result, the screw-type linear driving members 184 advance or retreat in specified directions, and the link bars 182 and 183 which are connected to the respective screw-type linear driving members 184 turn about the respective shafts 186.

Figure 15:
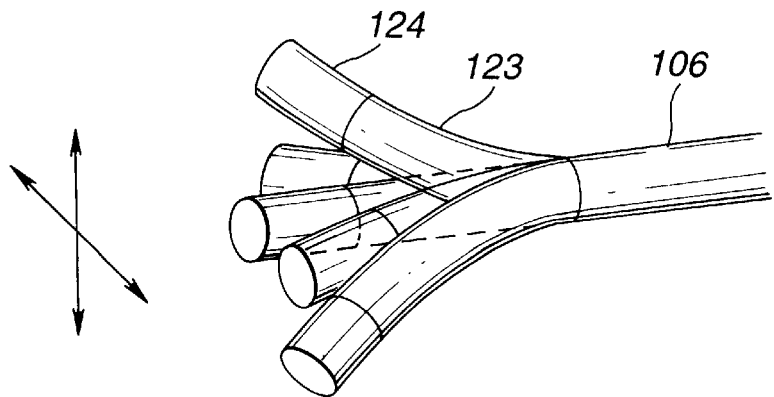

As a result, the up and don manipulation wires 126U and 126D which are connected to the link bar 182 and/or the right and left manipulation wires 126R and 126L move relatively to each other, whereby the position of the tip hard portion 124 with respect to the flexible tube front connecting piece 106 is changed. In this manner, the interval maintaining wire 181 is warped and the curving portion 123 can be curved freely in a desired direction as shown in FIG. 15.

As described above, the number of manipulation wires is increased and the interval maintaining wire 181 as the member for keeping the interval of the curving portion 123 at a given value is fixed to the tip hard portion 124 and the flexible tube front connecting piece 106. As the manipulation wires 126 are moved, the interval maintaining wire 181 is warped and the curving portion 123 is curved. In this manner, the curving control can be performed with high accuracy.

Further, since the interval of the curving portion 123 is kept at a given value by means Of the interval maintaining wire 181, the curving portion 123 can be curved at a small radius of curvature and a curve angle can be maintained in a stable manner.

Although in the second embodiment the number of manipulation wires is increased, the curving portion 123 may be formed by using the interval maintaining wire 181 and two manipulation wires 126. Even in this case, it is possible to curve the curving portion 123 to a desired direction by properly setting the arrangement positions of the interval maintaining wire 181 and the manipulation wires 126. A plurality of interval maintaining wires 181 may be provided. Further, instead of increasing the number of link mechanisms as the number of manipulation wires 126 is increased, the number of rack-pinion portions may be increased as the number of manipulation wires 126 is increased.

Next, a third embodiment will be described with reference to FIGS. 16 and 17. Although, for example, a light emitting diode (LED) is adopted as illumination means in the first embodiment, this modified example, instead of that, adopts a light source device provided in a drum portion and a light guide that transmits the light from this light source device and emits from an end surface of a tip portion of an insertion portion 121.

Figure 16:
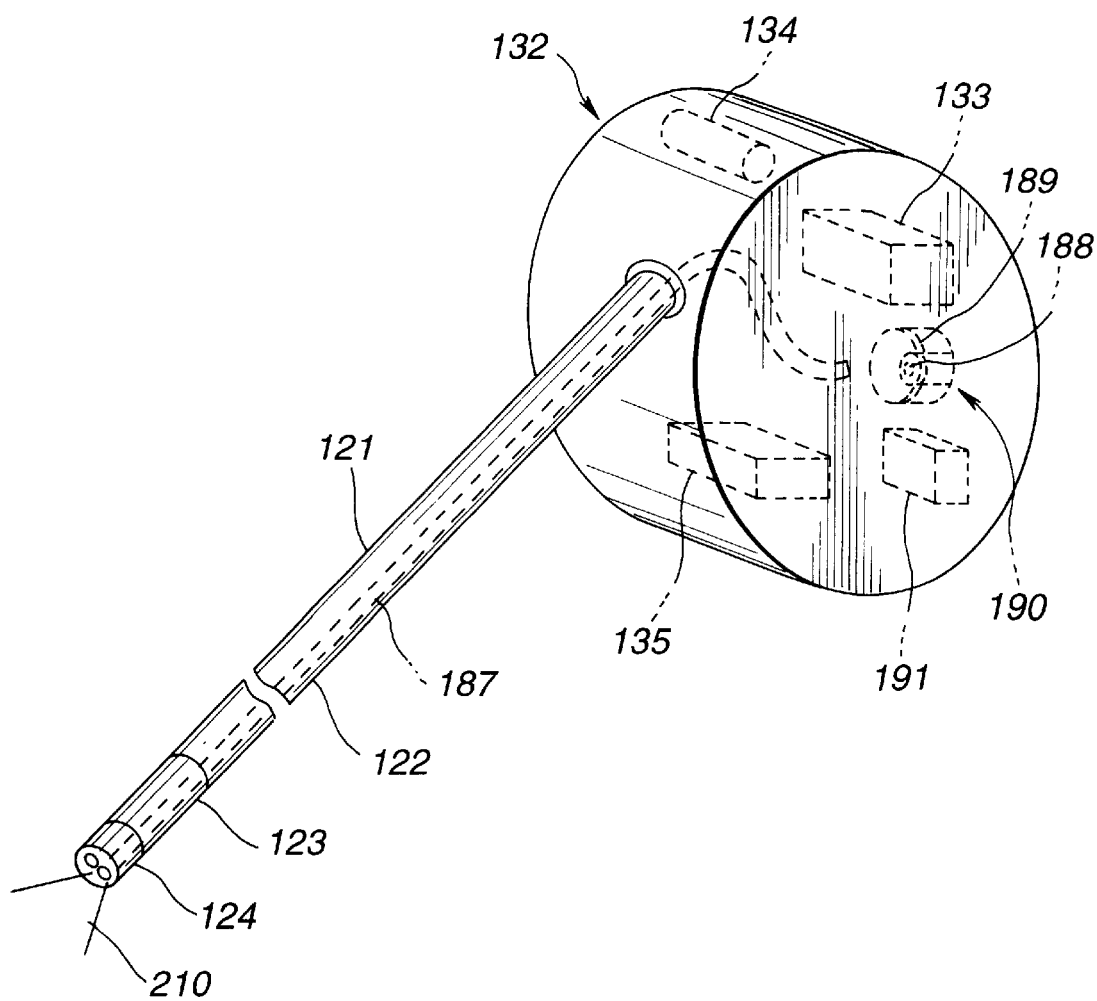
FIGS. 16–17 relate a third embodiment of the present invention.

As shown in FIG. 16, a light guide 187 transmitting illumination light is inserted in an insertion portion 121, the light guide 187 whose back end side is extended from a connecting portion of a proximal end of the insertion portion 121 into a drum portion 132.

In the drum portion 132, a light source device 190 comprising a lamp 188 and a condenser lens 189 is located with facing to the back end surface of this light guide 187. Furthermore, the light of the lamp 188 converged by the condenser lens 189 is supplied to the back end surface of the light guide 187. This light is transmitted by the light guide 187 and illumination light 210 is emitted from the end surface attached to an illumination window of a tip hard portion 124 of the insertion portion 121 to the front.

In addition, the lamp 188 is a xenon lamp, a halogen lamp, a metal halide lamp or the like that is commonly adopted as a light source for an endoscope apparatus.

Furthermore, a power supply apparatus 191 generating a DC power supply from an AC power supply is contained in the drum portion 132, the power supply apparatus 191 which supplies a lighting power supply voltage to the lamp 188 and necessary power supply voltages to a CCU 133, an actuator section 134, and a control circuit 135 that are located in the drum portion 132.

Figure 17:
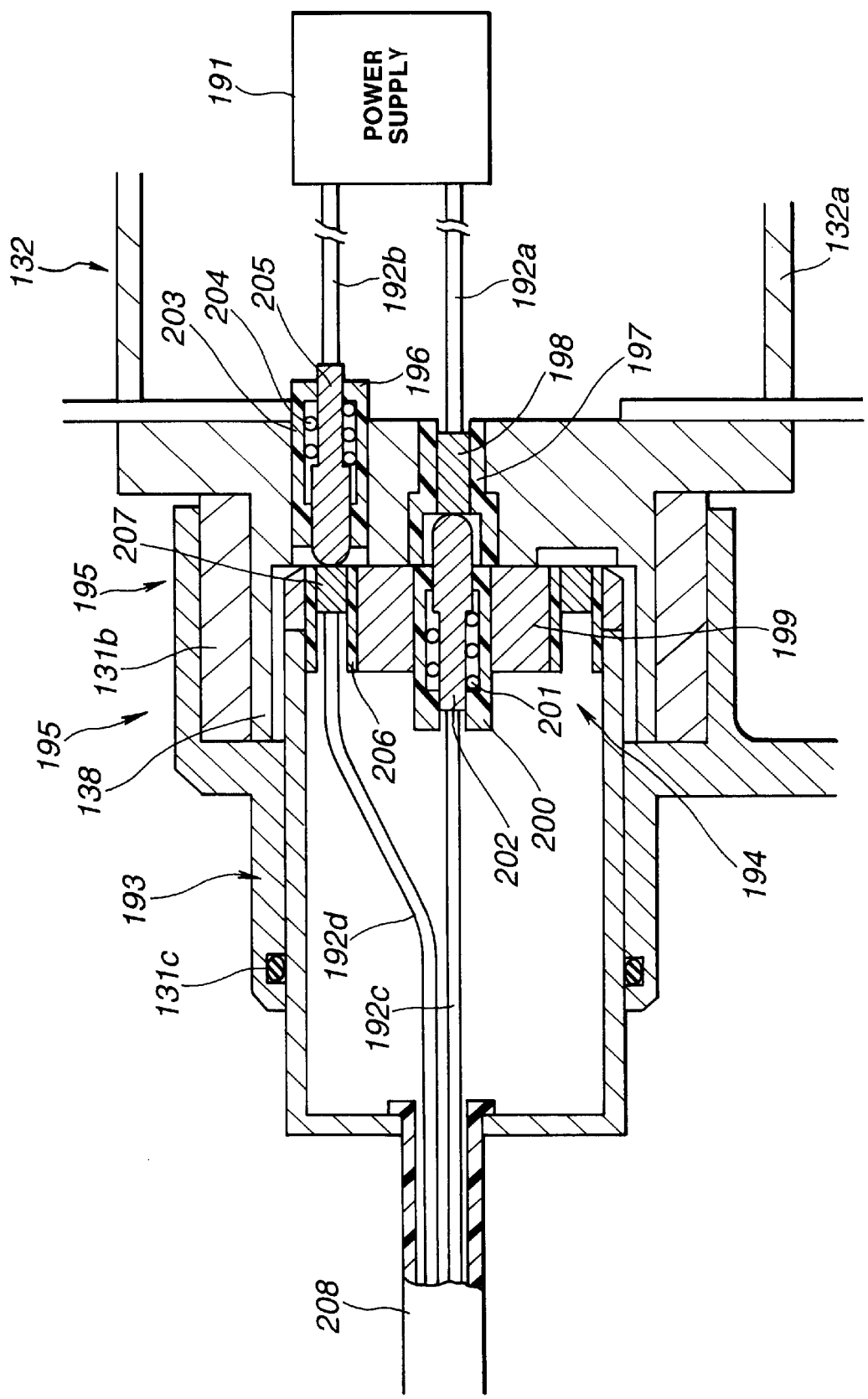

As shown in FIG. 17, power supply lines 192a and 192b connected to this power supply apparatus 191 are connected through a connecting section 195 of the power supply lines to power supply lines 192c and 192d outside the drum portion 132 respectively. Furthermore, the power supply apparatus 191 receives commercial power by connecting a plug at an end section of a power cable 208 of these power supply lines 192c and 192d to a receptacle of the commercial power.

The basic construction of the connecting section 195 of the power supply lines is the same as that of making a video signal contact electrode 139a and a ground terminal 139b contact to a video signal connecting terminal 142a and a ground contact electrode 142b respectively with a compression spring 171 at the connector connecting section 139 shown in FIG. 7.

Thus, the power supply line 192a is connected to an electrode 198 attached to a non-conductive holder 197 located on a rotation central axis in a side plate section 196 of the drum portion 132. This electrode 198 is connected to an electrode 202 that is attached to a non-conductive holder 199 provided on an electrode attaching plate 199 of a power supply line connector 194 and is energized by a compression spring 201 toward the electrode 198. This electrode 202 is connected to the power supply line 192c.

In addition, the power supply line 192b is attached to a non-conductive holder 203 provided at a position that is a peripheral side of the rotation central axis in the side plate section 196 of the drum portion 132, the line 192b which is connected to an electrode 205 energized by a compression spring 204 toward an electrode 207.

This electrode 205 is connected to the electrode 207 attached to a non-conductive holder 206 provided in a ring around the central position of the electrode attaching plate 199. The power supply line 192d is connected to this electrode 207.

In addition, a ring-shaped shaft portion 138 is convexly provided in the side plate section 196, and this shaft portion 138 is rotatably supported by a bearing portion 131b inside a power supply line connector receptacle 193. Furthermore, an O-ring 131c for water-tight is provided in the power supply line connector receptacle 193. Other construction is the same as that in the first embodiment, and hence description of that will be omitted.

Next, actions of this embodiment will be described.

Instead of the illumination by thew LED 154 in the first embodiment, light from the lamp 188 is supplied to the light guide 187 in this embodiment, and an observation portion is illuminated by the illumination light emitted from the end surface of this light guide 187, which is a different point.

In addition, another point of this embodiment that is different from the first embodiment is that AC power supplied from external commercial-power with the power cable 208 is converted to a DC power by the power supply apparatus 191 to supply it to the CCU 133 and the like. Therefore, this embodiment is suitable to long-time use.

Furthermore, it is also good to use this apparatus with the AC power supply or with the secondary battery with not using the AC power supply by building a secondary battery such as a lead battery, which is rechargeable, in the drum portion 132.

Subsequently, a fourth embodiment of the present invention will be described with reference to FIGS. 18–21. In the above-described embodiments, by fixing the tips of plural manipulation wire 126, which is inserted into the insertion portion 121 with being eccentric to the central axis and has superelastic property, to the tip hard portion 124 of the insertion portion 121 respectively and moving the back end portions of these manipulation wires 126 back and forth along the axis of the insertion portion with the motor 137 of the actuator section 134 in the drum portion 132, its driving force is transmitted by manipulation wires 126 and (a resin cover 125 having the superelastic property and covering) the curving portion 123 in their end side is curved. Nevertheless, in this embodiment, the curving portion is formed with a plurality of curving pieces (joint pieces) and the plurality of curving pieces are curved via manipulation wires.

Figure 18:
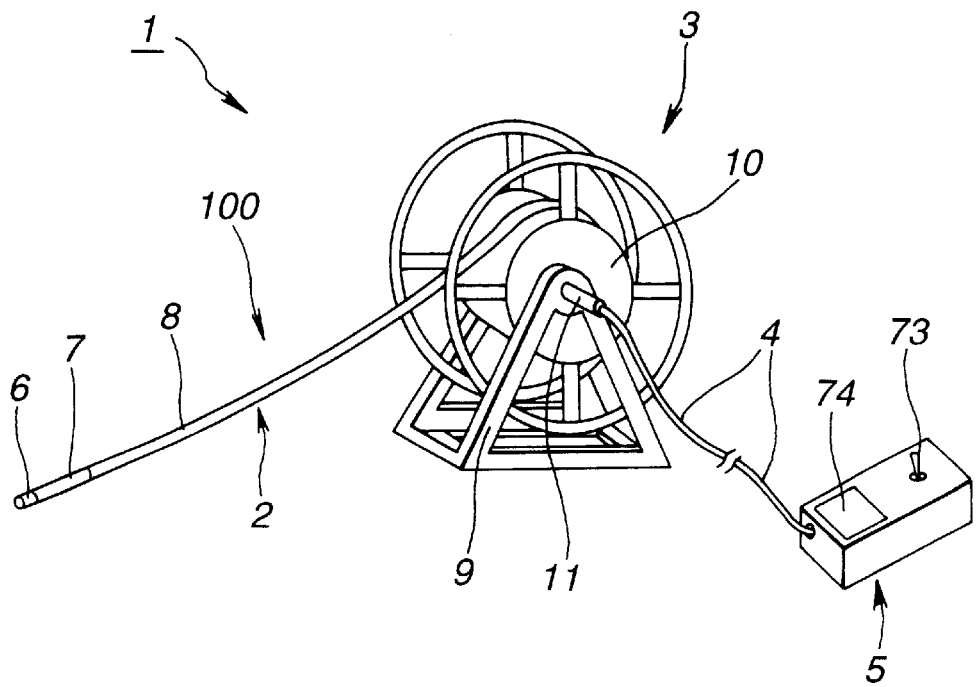

An endoscope apparatus 1 shown in FIG. 18 comprises an endoscope 100 having a long, flexible insertion portion 2, a drum device 3 to which a proximal end of this insertion portion 2 is connected, and a controller 5 that is connected to this drum device 3 through a cable 4.

The insertion portion 2 comprises a tip hard portion 6, a curving portion 7 that curves freely and makes the tip hard portion 6 curve to a desired direction, and a flexible tube 8 that is long and flexible.

The drum device 3 comprises a table 9, and a drum portion 10 that is supported by the table 9 and is freely rotatable. The insertion portion 2 is connected to the drum portion 10 and is wound on the outer circumference of the drum portion 10 when not used (when contained).

A cable 4 is connected to the drum device 3 via a connector 11 detachable from a shaft section supporting the drum portion 10. The cable 4 is slender and flexible, and internally has electric wires or optical communication cable, which are not shown, to transmit a control signal and a video signal. A controller 5 is connected to another end portion of this cable 4.

The controller 5 has a joy stick 73 as manipulation means for manipulating the curving manipulation of the curving portion 7, and a liquid crystal monitor 74 for displaying an image to be observed.

The connecting construction of a bearing portion and the connector 11 of the drum device 3 are the same as that in the first embodiment, and hence description of it will be omitted.

Figure 19:
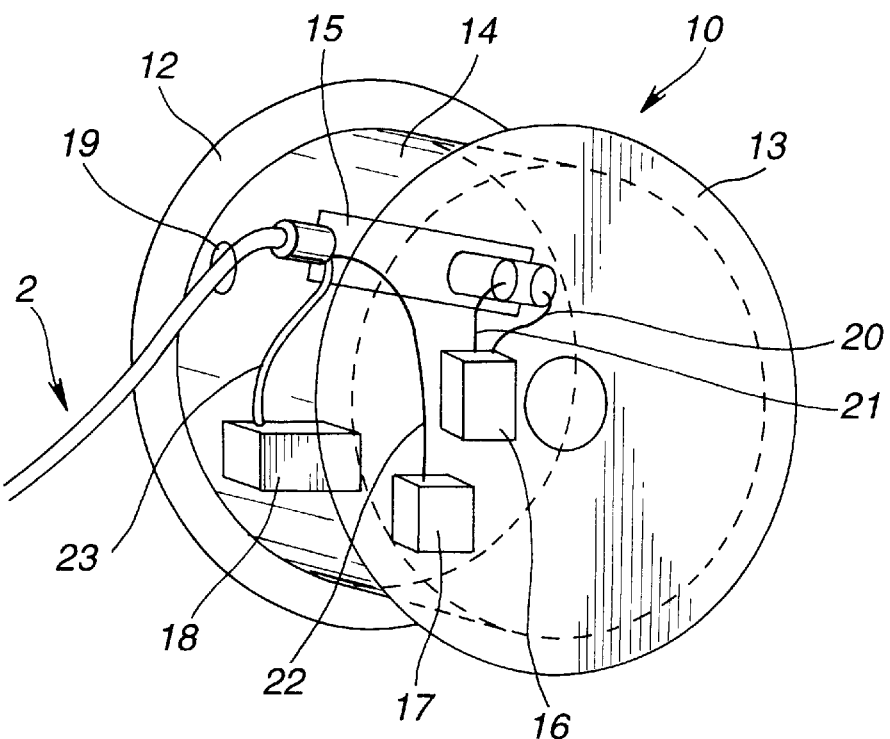

As shown in FIG. 19, the drum portion 10 comprises a cylindrical member 14 on which the insertion portion 2 is wound, and disc-shaped side plates 12 and 13 that are attached to openings in both sides of the cylindrical member 14. Furthermore, a sealed space (for example, water-tight and dust-tight by means of adhesion) is formed inside the cylindrical member 14.

An electric curving unit 15, a control circuit 16, a CCU 17, and a light source device 18 that are contained in this space inside the drum portion 10 are fixed to the side plate 12. In addition, similarly to the first embodiment, a battery, a balance weight, and the like can be provided in this space (not shown).

The insertion portion 2 is connected to the electric curving unit 15, and is drawn out from a through hole 19 bored in the cylindrical member 14. The electric curving unit 15 and control circuit 16 are connected via drive cables 20 and 21.

A signal line 22 inserted into the insertion portion 2 is connected to the CCU 17, and a light guide 23 is to the light source device 18.

The CCU 17 processes an image signal from a CCD that is transmitted via the signal line 22, and converts it to a TV signal to output the signal via the cable 4 to the liquid crystal monitor 74 as shown in FIG. 18.

The control circuit 18 controls the desired curving manipulation by controlling and driving a motor unit described later with an input signal by means of manipulation of the joy stick 73. The light source device 18 supplies light to the back end surface of the light guide 23, and the illumination light is emitted from the front end surface of the light guide 23 to an observation portion.

Figure 20A:
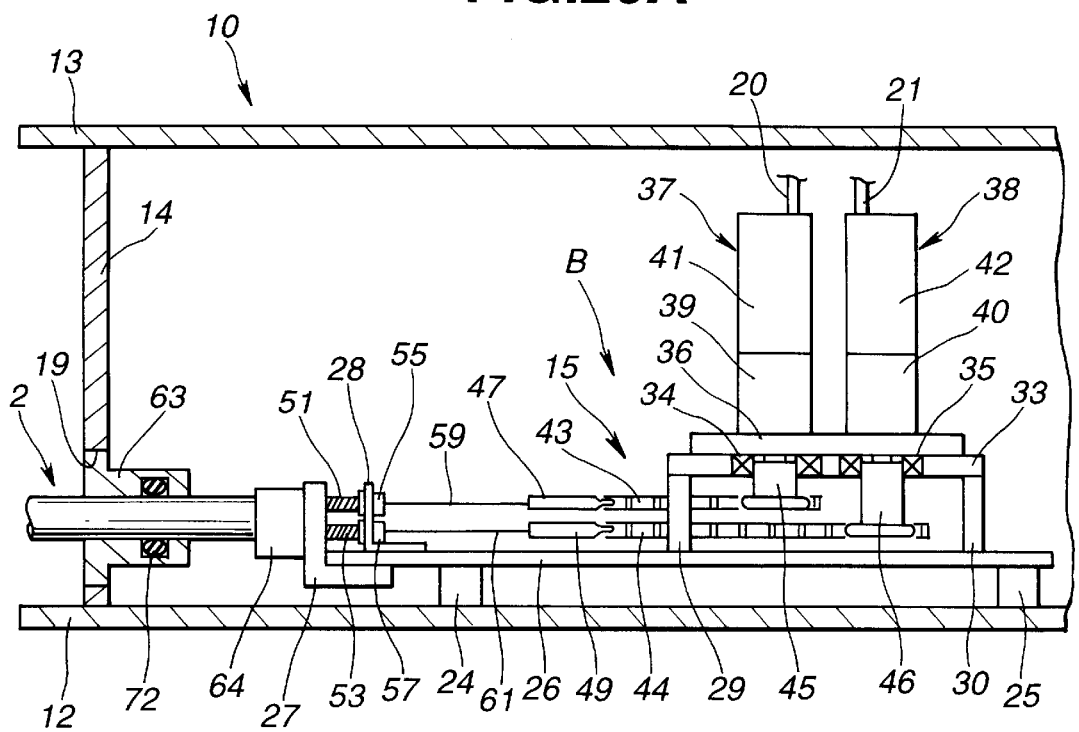
FIG. 20A is a side view of a motor unit.
Figure 20B:
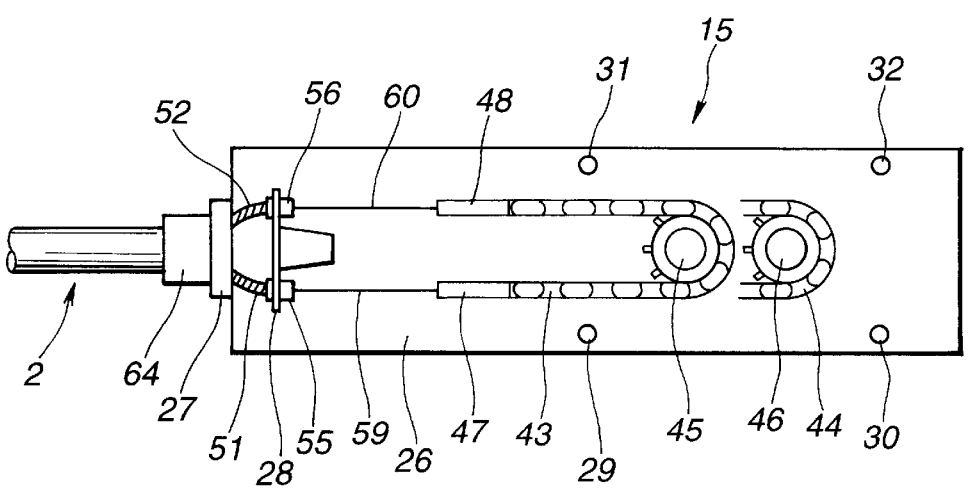
FIG. 20B is a plan from the B direction in FIG. 20A.

As shown in FIGS. 20A and 20B, the electric curving unit 15 is fixed (can be bonded) by, for example, a base plate 26 being screwed to the side plate 12 through spacers 24 and 25.

The electric curving unit 15 comprises a base plate 26, a fixing member 27 attached to an end portion (front end) of the base plate 26, a coil-pipe receptor 28, and a frame 33 fixed via supports 29–32.

Furthermore, a motor mount 36 is fixed to the frame 33 through bearings 34 and 35.

Motor units 37 and 38 are mounted to the motor mount 36. The motor units 37 and 38 comprise reduction gears 39 and 40 and motors 41 and 42 respectively.

Sprockets 45 and 46 are provided on output shafts of the motor units 37 and 38.

The sprockets 45 and 46 have teeth (see FIG. 20B) meshing with chains 43 and 44 in their outer circumferential surfaces, and are rotatably supported by the bearing 34 and 35. The chains 43 and 44 are wound around the sprockets 45 and 46, and are connected to the back ends of angle wires, both ends of which metal fittings 47–48 and 49–50 are attached to and which transmit the driving force and is described later.

A back connecting piece 64 at the back end of the insertion portion 2 is fixed to the fixing member 27, and connects the insertion portion 2 and electric curving unit 15. The back ends of coil pipes 51–52 and 53–54 are fixed to the coil pipe receptor 28 through coil pipe stoppers 55–56 and 57–58. The angle wires 59–60 and 61–62 transmitting the driving force from the motors 41 and 42 are inserted into the coil pipes 51–52 and 53–54.

When the joy stick 73 is manipulated, an input signal is inputted to the control circuit 16, and the control circuit 16 outputs to the motor units 37 and 38 a drive signal corresponding to this signal. Therefore, the motor units 37 and 38 are driven (the motors 41 and 42 rotate, and the reduction gears 39 and 40 reduce the speed and increase torque), and hence the output shaft rotates.

Then, since the sprockets 45 and 46 respectively mounted on the output shafts pull the angle wires 59–62 in respective directions via rotating chains 43 and 44, the curving portion is curved in the direction to which the angle wires are pulled.

The motor units, sprockets, chains, angle wires, and coil pipes are constructed in pairs respectively, and perform curving manipulation in the up/down and left/right directions.

If more accurate motor control is necessary, encoders may be attached to the motor units respectively.

An opening member 63 having a through hole 19 is fixed to the cylindrical member 14 with, for example, adhesive, and the insertion portion 2 is inserted into the through hole 19. In the inner circumferential surface of the opening member 63, an O-ring 72 is provided for the sake of water-tight and dust-tight, which prevent water and dust from infiltrating from the outside into the drum portion 10.

As shown in FIG. 21, an object lens 65, a CCD 66, a signal line 22, and a light guide 23 are provided inside the tip hard portion 6. The object lens 65 forms an image of an observation object on the CCD 66, and the CCD 66 performs photo electric conversion of the image to transmit an image signal to the CCU through the signal line 22. The light guide 23 casts the illumination light to the observation object.

The signal line 22 and light guide 23 are inserted into the insertion portion 2 and reach the inside of the drum portion 10.

The curving portion 7 is provided in the back end of the tip hard portion 6, and this curving portion 7 is formed by a plurality of ring-shaped joint pieces 67 being rotatably connected by rivets 68 as pivot sections (rotatable supports). These joint pieces are covered by a rubber tube 69.

Cylindrical wire receptors 70 are provided at positions corresponding to the up/down and left/right in the inner circumferential surface of the joint pieces 67, and in this space the angle wires 59–62 (only the angle wires 59 and 60 located in the up/down direction are shown in FIG. 21) are slidably inserted. Thus, the angle wires 59–62 are inserted along the position eccentric to the central axis of the curving portion 7.

The front ends of the angle wires 59–62 are fixed at the up/down and left/right positions of the back end section of the tip hard portion 6, and the curving portion 7 can be curved by pulling the angle wires corresponding to respective directions.

In addition, the joint pieces 67 constructs the curving portion 7 with their number being increased according to the desired maximum curving angle (the number is not limited to the number of the joint pieces 67 in FIG. 21).

The long flexible-tube 8 is extended to the back end of the curving portion 7. The coil pipes 51–54 (only the coil pipes 51 and 52 are shown in FIG. 21) are provided inside this flexible tube 8. The coil pipes 51–54 are fixed to the front end portion of the flexible tube 8 with, for example, brazing and the like. Inside these pipes the angle wires 59–62 are slidably inserted.

The coil pipes 51–54 and angle wires 59–62 are inserted into the flexible tube 8 and reach the electric curving unit 15.

The insertion portion 2 is sheathed for protection by an external blade 71 made of a wire mesh.

Next, actions of this embodiment will be described.

In the endoscope apparatus 1, the insertion portion 2 is wound up by the drum device 3 before it is used (for example, stored or transported).

As the preparation of inspection work, that is, setup of the endoscope apparatus 1, the insertion portion 2 is drawn out by rotating the drum device.

In this case, the work for connecting the endoscope and light source device and/or CCU that is performed in the previous embodiment is not necessary because they are already connected in the drum device in this embodiment.

A detachable controller 5 is connected to the drum device 3 so that manipulation of the curving manipulation and observation with the liquid crystal monitor 74 can be performed.

The manipulation of the curving operation is performed by controlling the rotary motion of the motors 41 and 42 through the control circuit 18 be means of manipulating the joy stick 73.

After inspection, the controller 8 is disconnected, and the insertion portion is wound up on the cylindrical member 14 of the drum device 3.

This embodiment has the following effects.

Even if the insertion portion 2 is long, it is possible to compactly contain the insertion portion 2 by winding the insertion portion 2 on the drum device 3, and hence it is easy to store and transport the endoscope apparatus.

Since the drawing and winding of the insertion portion 2 are simple work, preparation and clearance of an inspection can be easily performed in a short time.

Since the peripheral equipment such as the light source device 18 and CCU 17 is contained inside the drum device 3, the entire system is compact and is unified. Owing to this, not only storage and transportation are easy, but also installation of the endoscope apparatus is easy even if the place at the time of inspection is narrow.

Conventionally, although the CCU and electric curving unit are packaged separately, they are contained inside the drum device 3 in this embodiment. Therefore, respective sheaths become unnecessary, and hence it also becomes possible to reduce production cost.

In addition, since the light source device 18 and CCU 17 are already connected in the drum device 3, it is possible to complete the preparation and clearance of the inspection in a short time. Furthermore, incorrect connection can be prevented (failure of equipment can be prevented).

Moreover, owing to the electric curving, curving manipulation can be performed more lightly than the manual curving. Hence, work of the endoscopy becomes easy, and inspector's fatigue can be reduced.

Since a curving mechanism is not built in the controller 5, it is possible to easily realize small size, light weight, and optimum shape (conventionally, an electric or manual curving mechanism is provided inside the controller).

Next, a modified example of the fourth embodiment will be described with referring to FIG. 22. In this modified example, the fixed location of the electric curving unit is different from that in the fourth embodiment.

Figure 22:
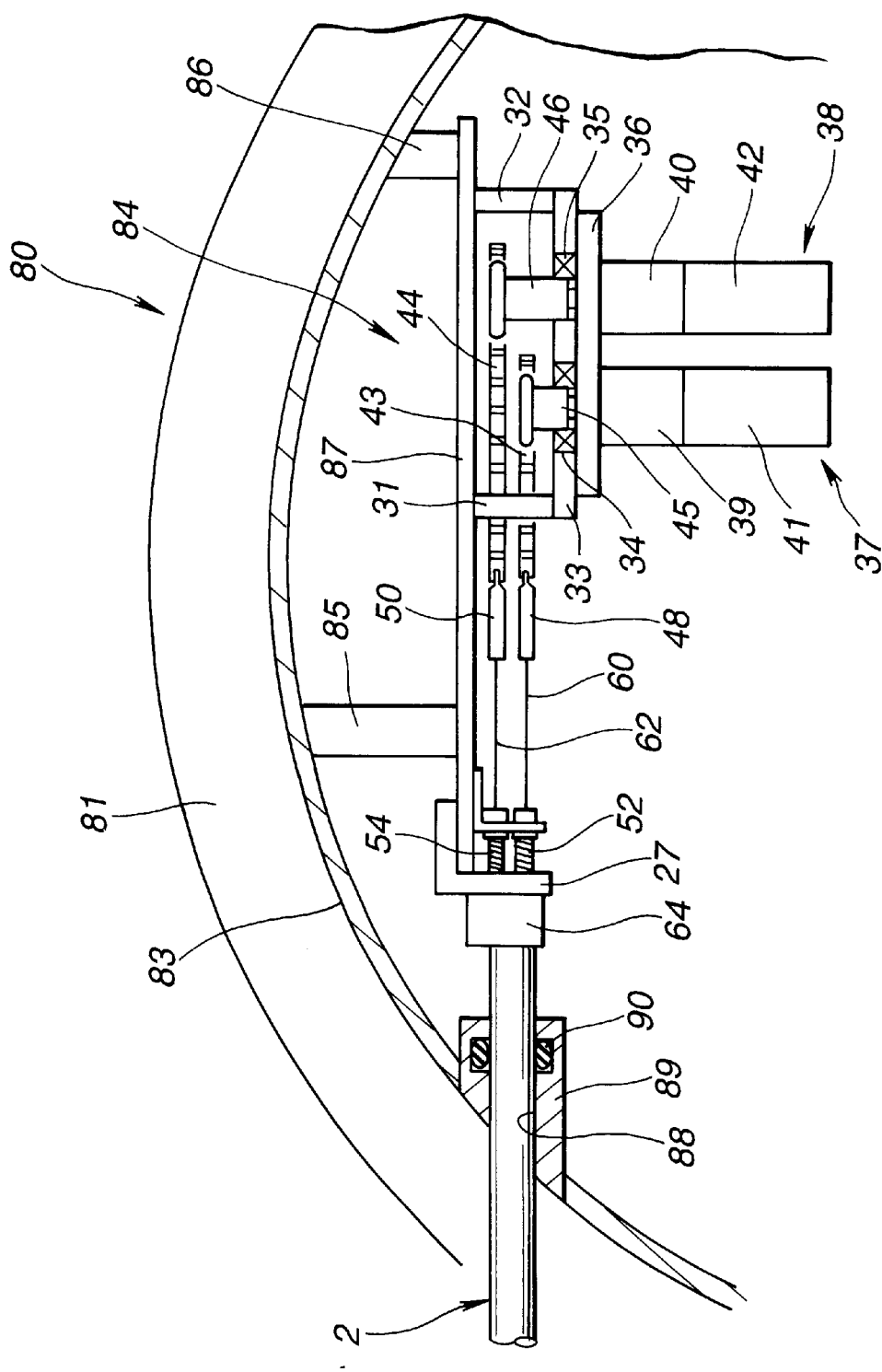

As shown in FIG. 22, a drum portion 80 comprises a cylindrical member 83, and two side plates 81 and 82 (only one side plate 81 is shown in FIG. 22), and internally has a space for fixing an electric curving unit 84.

The electric curving unit 84 is fixed to the cylindrical member 83 by, for example, a base plate 26 being screwed (or bonded) to a base plate 87 through spacers 85 and 86.

The cylindrical member 83 has an opening member 89 having a through hole 88 nearby a mounted location of the electric curving unit 84.

The opening member 89 has water-tight and dust-tight construction by means of adhesive and the like and is fixed to the cylindrical member 83. The insertion portion 2 connected to the electric curving unit 84 is drawn from the through hole 88 to the outside.

Inside the through hole 88, an O-ring 90 is provided for the sake of water-tight and dust-tight between the insertion portion 2 and through hole 88.

The control circuit, CCU, light source device, and the like that are not shown, similarly to those in the fourth embodiment, are fixed to either of two side plates 81 and 82.

Actions of this embodiment are the same as those in the fourth embodiment.

In addition, in this embodiment, since the electric curving unit 84 is fixed to the cylindrical member 83, a space by the side plates becomes large, and hence it becomes possible to allocate the larger spaces to the control circuit, CCU, light source device, battery, and balance weight respectively. Alternatively, the size of the drum portion can be reduced. Others are the same as those in the fourth embodiment.

Next, a fifth embodiment of the present invention will be described with reference to FIGS. 23–25.

In the above-described embodiments, motors rotating by applying a drive signal as electric drive means are used. Nevertheless, this embodiment constructs an electric curving unit 15 linearly driving (moving) angle wires electrically with using solenoids and plungers. Thus, this embodiment adopts linear drive means for electrically moving plungers.

In addition, the same numerals will be assigned to the parts that are the same as those in the fourth embodiment, and they will be described.

Furthermore, for the sake of easy understanding of description in this embodiment, a case of, for example, curving to two directions, that is, up and down directions (or left and right directions) will be described.

Solenoids 91 and 92 are fixed to the base plate 26 at the location facing to coil pipe stops 55 and 56 fixed to a coil pipe receptor 28 in the front end side of the base plate 26. Plungers 93 and 94 are movably located in the hollow portions of the solenoids 91 and 92 respectively.

Figure 23:
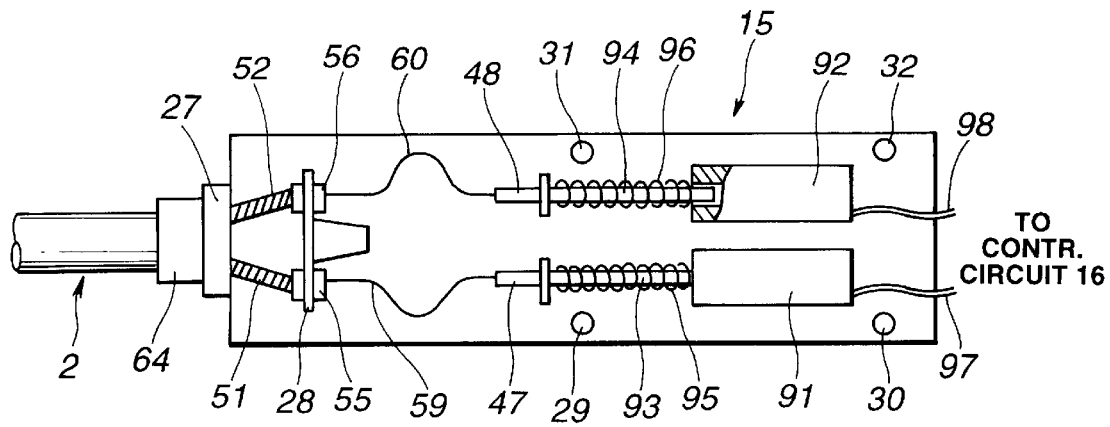
FIGS. 23–25 relate to a fifth embodiment of the present invention.

The plungers 93 and 94 are energized to the direction separate from the solenoids 91 and 92 (the direction where the plungers are drawn out) (the state in FIG. 23).

In addition, the back ends of the angle wires 59 and 60 are connected to the front ends of the solenoids 91 and 92 via metal fittings 47 and 48.

The solenoids 91 and 92 are connected to the control circuit 16 via signal lines 97 and 98. If the joy stick 73 in FIG. 18, for example, is inclined forward, a drive current corresponding to its inclined angle is made to flow in the solenoid 91. Then, the solenoid 91 pulls the plunger 93 into the hollow portion of the solenoid 91, while the curving portion 7 can be made to curve, for example, upward by moving the angle wires 59 backward.

Other construction is the same as that in the fourth embodiment.

Next, operation of this embodiment will be described.

FIG. 23 shows a state of the curving portion being free, that is, a state of the electric curving unit 15 without load where the angle wires have no load. In this state, the solenoids 91 and 92 are not conductive, and the plungers 93 and 94 are pulled out at the maximum from the solenoids 91 and 92 by the coil springs 95 and 96.

At this time, play arises at the angle wires 59 and 60, and the curving portion 7 becomes free. The curving portion 7 is made to fundamentally become this state when power is turned off, the insertion portion 2 is contained to the drum portion 10, and the insertion portion is pulled out from the object under inspection.

In addition, this state is optionally selectable by the operation from the controller 5.

Figure 24:
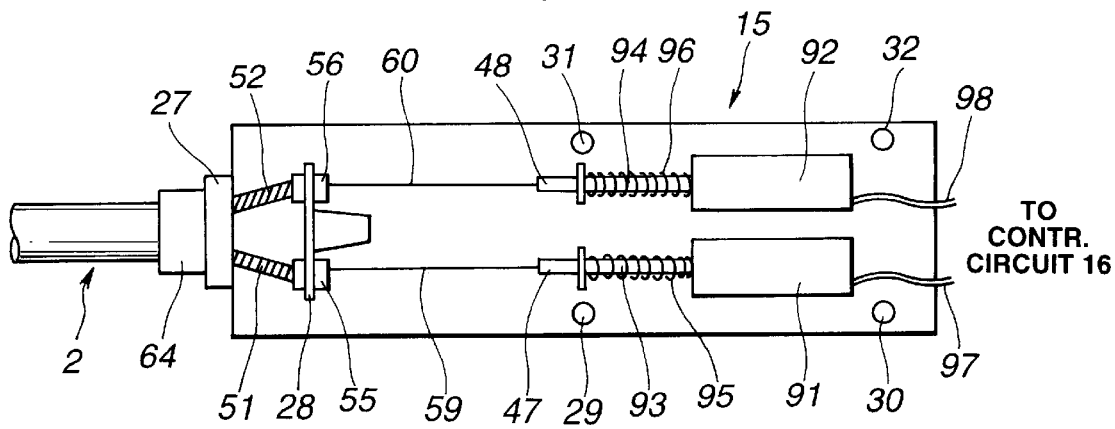

FIG. 24 shows the state of a curving angle being zero degree, that is, a neutral state of curving. This state is realized by the control circuit 16 controlling values of the currents flowing respective solenoids 91 and 92 on the basis of a curving neutral state instruction from the controller 5 and the like and making tensile amounts of respective angle wires 93 and 94 uniform.

Figure 25:
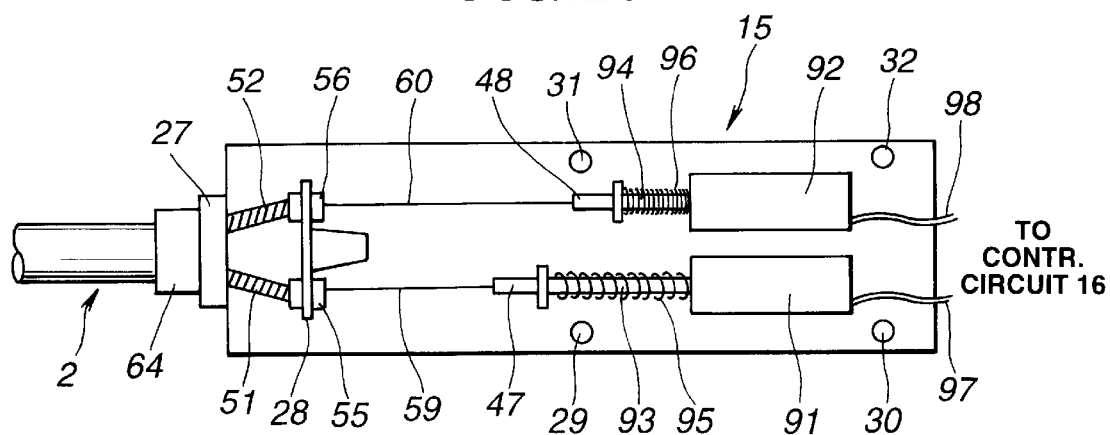

FIG. 25 shows an example at a state where the curving manipulation is performed to a pair of solenoids 91 and 92. By inclining the joy stick 73 of the controller 5 to the direction to be curved, the control circuit 16 controls currents flowing in respective solenoids 91 and 92 on the basis of its curving angle instruction. The plunger 93 of the solenoid 92 is pulled in according to the curving angle instruction, and another solenoid is pushed out in correspondence to it.

Owing to this, it is possible to curve the curving portion to the direction corresponding to the instruction and at the curving angle corresponding to the instruction. Thus, it is possible to curve the curving portion in an optional direction and at an optional angle by the curving manipulation.

In addition, although FIGS. 23–25 show a pair of electric curving units 15 corresponding to a case of curving to two directions, it is apparent that this invention can be applied to a case of curving to four directions by using two pairs of electric curving units 15.

Effects of this embodiment are the same as those in the fourth embodiment.

Furthermore, DC motors driven by DC drive signals, stepping motors driven by pulse-like drive signals, and ultrasonic motors driven by high-frequency drive signals can be used as motors constructing the curving drive means. Moreover, means for linearly driving an object electrically is not limited to solenoids and plungers, but linear motors and the like can be used.

In addition, embodiments constructed by partially combining respective embodiments described above also belong to the present invention.

What is claimed is:

1. An endoscope apparatus, comprising:

an elongate, flexible insertion portion that has a curving portion capable of curving and that can be inserted into a cavity;

a drum portion connected to the proximal end of said insertion portion, said drum portion having a rotatable drum body and a drum fulcrum by which said drum body is rotatably held, said drum body having a cylindrical portion and side portions, said side portions configured to block openings in both sides of said cylindrical portion, said cylindrical portion containing a through hole in which the proximal end of said insertion portion is passed therethrough;

an illumination optical system provided in a tip portion of said insertion portion and configured to emit illumination light from a light source device contained within said drum body;

an imaging optical system provided in said tip portion of said insertion portion and configured to provide images of an object illuminated by said illumination optical system;

a signal processing device, contained within said drum body, configured to perform signal processing functions on images from said imaging optical system and to generate a video signal;

manipulation wires that are inserted in an axial direction of said insertion portion and that make said curving portion curve by moving in the axial direction;

a drive motor that is provided on at least one of said cylindrical portion and side portions of said drum body, said drive motor making said curving portion curve by moving said manipulation wires;

a fixing member provided in said drum body, by which the position of said drive motor is fixed with respect to the position of the proximal end of said insertion portion, said fixing member being fixed to at least one of said cylindrical portion and said side portion of said drum body;

a signal cable which is extended from the inside to the outside through said drum body and said drum fulcrum; and curving manipulation means for performing curving manipulation of said curving portion by controlling drive motion of said drive motor, said curving manipulation means being connected to an end of said signal cable which extends from said drum portion.

2. An endoscope apparatus according to claim 1, wherein an imaging device performing photo electric conversion is located at an imaging position of said imaging optical system in said tip portion of said insertion portion.

3. An endoscope apparatus according to claim 2, further comprising display means for displaying an image photo-electrically converted by said imaging device.

4. An endoscope apparatus according to claim 3, wherein said display means is located outside said drum portion.

5. An endoscope apparatus according to claim 3, wherein said display means is located outside said drum portion and is detachably connected to said drum portion via a cable.

6. An endoscope apparatus according to claim 1, wherein said drum portion is rotatably held by a drum fulcrum.

7. An endoscope apparatus according to claim 6, wherein said drum portion is provided with a connector portion that is provided on a rotation central axis and is rotatably held by the drum fulcrum for being detachably connected to a device located outside said drum portion.

8. An endoscope apparatus according to claim 7, wherein said curving manipulation means is connected to said connector portion.

9. An endoscope apparatus according to claim 7, wherein a cable connects an external commercial power supply to said connector portion.

10. An endoscope apparatus according to claim 1, wherein said curving portion has a flexible tube member covering said curving portion, said manipulation wires are inserted along a plurality of positions eccentric to a central axis of said tube member, and tip ends of said manipulation wires are fixed to said tip portion of said insertion portion.

11. An endoscope apparatus according to claim 10, wherein at least one of said flexible tube member and said manipulation wires is constructed by at least one member having superelastic properties.

12. An endoscope apparatus according to claim 1, wherein said curving portion has a plurality of ring-shaped pieces rotatably supported with each other at pivots along an axial direction of said curving portion and tips of said manipulation wires are fixed to a tip side of said plurality of ring-shaped pieces.

13. An endoscope apparatus according to claim 1, wherein said illumination optical system has a light emitting diode.

14. An endoscope apparatus according to claim 1, wherein a light guide transmitting illumination light is inserted inside said insertion portion.

15. An endoscope apparatus according to claim 1, wherein a power supply is located inside said drum portion.

16. The endoscope apparatus of claim 15, wherein the power supply is a battery.

17. The endoscope apparatus of claim 15, wherein the power supply is a DC power supply that converts an AC power source to DC power.

18. An endoscope apparatus according to claim 1, wherein a control circuit that controls operation of said drive motors according to curving manipulation of said curving manipulation means is located in said drum portion.

19. An endoscope apparatus according to claim 1, wherein a plurality of drive motors are located in said drum portion.

20. An endoscope apparatus according to claim 1, wherein said cylindrical portion has an opening through in which a proximal end of said insertion portion passes from an outside of said cylindrical portion to an inside of said cylindrical portion.

21. An endoscope apparatus according to claim 20, wherein said opening in which the proximal end of said insertion portion is inserted is sealed to form a water-tight seal.

22. An endoscope apparatus according to claim 1, wherein said curving manipulation means is detachably connected to said drum portion via said signal cable.

23. An endoscope apparatus comprising:
an elongate, flexible insertion portion that has a curving portion capable of curving and that can be inserted into a cavity;
an illumination optical system emitting illumination light and an imaging optical system imaging an object illuminated by said illumination optical system, both of which are provide in a tip portion of said insertion portion;
a drum portion connected to the proximal end of said insertion portion, said drum portion having a rotatable drum body and a drum fulcrum by which said drum body is rotatably held, said drum body having a cylindrical portion and side portions, said side portions configured to block openings in both sides of said cylindrical portion, said cylindrical portion containing a through hole in which the proximal end of said insertion portion is passed therethrough;
manipulation wires that are inserted in an axial direction of said insertion portion and that make said curving portion curve by moving in the axial direction;
a drive motor that is provided on at least one of said cylindrical portion and side portions of said drum body, said drive motor making said curving portion curve by moving said manipulation wires;
a signal cable which is extended from the inside to the outside through said drum body and said drum fulcrum; and
curving manipulation means for performing curving manipulation of said curving portion by controlling drive motion of said drive motor, said curving manipulation means being connected to an end of said signal cable which extends from said drum portion,
wherein said curving portion includes a flexible tube member having superelastic properties and covering said curving portion, said manipulation wires being inserted along a plurality of positions eccentric to a central axis of said tube member, and tip ends of said manipulation wires being fixed to said tip portion of said insertion point.

24. An endoscope apparatus, comprising:
an elongate, flexible insertion portion that has a curving portion capable of curving and that can be inserted into a cavity;
a drum portion connected to the proximal end of said insertion portion, said drum portion having a rotatable drum body and a drum fulcrum by which said drum body is rotatably held, said drum body having a cylindrical portion and side portions, said side portions configured to block openings in both sides of said cylindrical portion, said cylindrical portion containing a through hole in which the proximal end of said insertion portion is passed therethrough;
an illumination optical system provided in a tip portion of said insertion portion and configured to emit illumination light from a light source device contained within said drum body;
an imaging optical system provided in said tip portion of said insertion portion and configured to provide images of an object illuminated by said illumination optical system;
a signal processing device, contained within said drum body, configured to perform signal processing functions on images from said imaging optical system and to generate a video signal;

manipulation wires that are inserted in an axial direction of said insertion portion and that make said curving portion curve by moving in the axial direction;

an electric drive means that is stored in said drum body, said electric drive means making said curving portion curve by moving said manipulation wires;

a fixing member provided in said drum body, by which the position of said electric drive means is fixed with respect to the position of the proximal end of said insertion portion, said fixing member being fixed to at least one of said cylindrical portion and said side portion of said drum body;

a signal cable which is extended from the inside to the outside through said drum body and said drum fulcrum; and curving manipulation means for performing curving manipulation of said curving portion by controlling drive motion of said electric drive means, said curving manipulation means being connected to an end of said signal cable which extends from said drum portion.

25. An endoscope apparatus according to claim 24, wherein said electric drive means includes a motor rotated by a drive signal.

26. An endoscope apparatus according to claim 24, wherein said electric drive means includes linear moving means for linearly moving said manipulation wires by a drive signal.

27. An endoscope apparatus according to claim 26, wherein said linear moving means includes an electric-driven plunger linearly moving said manipulation wires by said drive signal.

28. An endoscope apparatus according to claim 24, wherein an imaging device performing photo electric conversion is located at an imaging position of said imaging optical system in said tip portion of said insertion portion.

29. An endoscope apparatus according to claim 27, further comprising display means for displaying an image photoelectrically converted by said image device.

30. An endoscope apparatus according to claim 29, wherein said display means is located outside said drum portion.

31. An endoscope apparatus according to claim 24, wherein said curving manipulation means is detachably connected to said drum portion via said signal cable.

32. An endoscope apparatus according to claim 24, wherein said curving portion has a flexible tube member covering said curving portion, said manipulation wires are inserted along a plurality of positions eccentric to a central axis of said tube member, and tip ends of said manipulation wires are fixed to said tip portion of said insertion portion.

33. An endoscope apparatus according to claim 32, wherein at least one of said flexible tube member and said manipulation wires is constructed by at least one member having superelastic properties.

34. An endoscope apparatus according to claim 24, wherein said curving portion has a plurality of ring-shaped pieces rotatably supported with each other at pivots along an axial direction of said curving portion and tips of said manipulation wires are fixed to a tip side of said plurality of ring-shaped pieces.

35. An endoscope apparatus according to claim 24, wherein said drum portion is rotatably held by a drum fulcrum.

36. An endoscope apparatus, comprising:

an elongate, flexible insertion portion that has a curving portion capable of curving and that can be inserted into a cavity;

an illumination optical system emitting illumination light and an imaging optical system imaging an object illuminated by said illumination optical system, both of which are provide in a tip portion of said insertion portion;

a drum portion connected to the proximal end of said insertion portion, said drum portion having a rotatable drum body and a drum fulcrum by which said drum body is rotatably held, said drum body having a cylindrical portion and side portions, said side portions configured to block openings in both sides of said cylindrical portion, said cylindrical portion containing a through hole in which the proximal end of said insertion portion is passed therethrough, said insertion portion being wound around the outer surface of said drum body when said drum body rotates;

manipulation wires that extend from said drum portion to said insertion point and are inserted in an axial direction of said insertion portion and that make said curving portion curve by moving in the axial direction;

an electric drive means that is stored in said drum body, said electric drive means making said curving portion curve by moving said manipulation wires;

a signal cable which is extended from the inside to the outside through said drum body and said drum fulcrum; and curving manipulation means for performing curving manipulation of said curving portion by controlling drive motion of said electric drive means, said curving manipulation means being connected to an end of said signal cable which extends from said drum portion, wherein said curving portion includes a flexible tube member having superelastic properties and covering said curving portion, said manipulation wires being inserted along a plurality of positions eccentric to a central axis of said tube member, and tip ends of said manipulation wires being fixed to said tip portion of said insertion point.

* * * * *